US008211652B2

(12) United States Patent
Hirsch

(10) Patent No.: US 8,211,652 B2
(45) Date of Patent: Jul. 3, 2012

(54) FSTL-1 AS A BIOMAKER OF INFLAMMATION

(75) Inventor: Raphael Hirsch, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 12/864,709

(22) PCT Filed: Jan. 29, 2009

(86) PCT No.: PCT/US2009/032429
§ 371 (c)(1),
(2), (4) Date: Nov. 1, 2010

(87) PCT Pub. No.: WO2009/097424
PCT Pub. Date: Aug. 6, 2009

(65) Prior Publication Data
US 2011/0045507 A1 Feb. 24, 2011

Related U.S. Application Data

(60) Provisional application No. 61/024,487, filed on Jan. 29, 2008.

(51) Int. Cl.
*G01N 33/53* (2006.01)
(52) U.S. Cl. .......................................... 435/7.1; 435/7.2
(58) Field of Classification Search .................. None
See application file for complete search history.

(56) References Cited

U.S. PATENT DOCUMENTS

| | | | |
|---|---|---|---|
| 5,143,854 A | 9/1992 | Pirrung et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,661,028 A | 8/1997 | Foote |
| 5,800,992 A | 9/1998 | Fodor et al. |
| 6,410,232 B1 | 6/2002 | Holtzman |

FOREIGN PATENT DOCUMENTS

| | | |
|---|---|---|
| EP | 0373203 | 6/1990 |
| EP | 0785280 | 7/1997 |
| WO | WO95/21265 | 8/1995 |
| WO | WO96/31622 | 10/1996 |
| WO | WO97/10365 | 3/1997 |
| WO | WO97/27317 | 7/1997 |
| WO | WO2004/018522 | 3/2004 |
| WO | WO2005/032328 | 4/2005 |

OTHER PUBLICATIONS

Tanaka et al. (International Immunology 1998 vol. 10, p. 1305-1314).*
Miyamae et al. (J. Immunology 2006 vol. 177, p. 4758-4762).*
Brown et al., "Control of I kappa B-alpha proteolysis by site-specific, signal-induced phosphorylation", Science. 267:1485-1488 (1995).
Chu et al., "IFNgamma deficient C57BL/6 (H-2b) mice develop collagen induced arthritis with predominant usage of T cell receptor μbeta6 and Vbeta8 in arthritic joints", Annals of the Rheumatic Diseases. 62:983-990 (2003).
Clutter et al., "Follistatin like protein-1 is a marker of inflammation", The Journal of Immunology, 178:131.31 (2007).
Clutter et al., "Follistatin-Like Protein 1 Promotes Arthritis by Up-Regulating IFN-γ[1]", The Journal of Immunology, 182: 234-239 (2009).
Constantinescu, et al., "Antibodies against IL-12 prevent superantigen-induced and spontaneous relapses of expiremental autoimmune encephalomyelitis", J Immunol. 161:5097-104 (1998).
Current Protocols in Molecular Biology (F.M. Ausubel, et al., eds., 1987 including supplements through 2001). Table of contents.
Current Protocols in Nucleic Acid Chemistry, John Wiley & Sons, NY, 2000. Table of Contents retrieved on line from Wiley Online Library on Feb. 24, 2012 http://onlinelibrary.wiley.com/book/10.1002/0471142700/toc.
Diagnostic guidelines for Kawasaki disease. *Circulation.* 103(2):335-336 (2001).
Ehara et al., "Follistatin-related protein gene (FRP) is expressed in the synovial tissues of rheumatoid arthritis, but its polymorphisms are not associated with genetic susceptibility", Clin Exp Rheumatol. 22:707-712 (2004).
Gett et al., "T cell fitness determined by signal strength", Nat Immunol. 4:355-360 (2003).
Hambrock, et al., Journal of Biological Chemistry, 279, 11727, (Mar. 19, 2004).
Hardy et al., "Construction of adenovirus vectors through Cre-lox recombination", J Virol. 71(3):1842-1849 (1997).
Harlow and Lane (1988) Antibodies, a Laboratory Manual, Cold Spring Harbor Publications, NY. Table of contents.
Harlow and Lane (1999) Antibodies, a Laboratory Manual, Cold Spring Harbor Press, NY. (Beaucage, et al., eds). Table of contents.
Hughes et al., "Induction of T cell anergy in an experimental model of autoimmunity using non-mitogenic anti-CD3 monoclonal antibody", J. Immunol. 153(7):3319-3325 (1994).
Johnston et al., "Regulation, of a multigenic invasion programme by the transcription factor, AP-1:re-expression of a doWn-regulated gene, TSC-36, inhibits invasion", Oncogene. 19(47): 5348-58 (2000).
Kawabata et al., "Ameliorative effects of follistatin-related protein/TSC-36/FSTL1 on joint inflammation in a mouse model of arthritis", Arthritis Rheum. 50(2):660-668 (2004).
Kim et al., "TNF type 2 receptor (p75) lowers the threshold of T cell activation", J. Immunol 167(12):6812-6820 (2001).

(Continued)

Primary Examiner — Jacob Cheu
(74) Attorney, Agent, or Firm — Baker Botts, L.L.P.

(57) ABSTRACT

The invention provides methods and kits for diagnosing severity of particular types of inflammatory diseases, such as rheumatic diseases, by assessing protein levels of follistatin-like protein 1 (FSTL-1). The level of FSTL-1 protein present in the serum or synovial fluid of individuals suspected of having certain inflammatory disease (e.g, rheumatoid arthritis) is positively correlated with the severity of the disease.

4 Claims, 17 Drawing Sheets

OTHER PUBLICATIONS

Kwak et al., "Reciprocal cross-talk between RANKL and interferon-gamma-inducible protein 10 is responsible for bone-erosive experimental arthritis", *Arthritis Rheum.* 58(5):1332-1342 (2008).

Kubo et al., "Characterization of a monoclonal antibody which detects all murine a[i T cell receptors", *J. Immunol.* 142(8):2736-2742 (1989).

Mashimo et al., "Decrease in the expression of a novel TGF beta1-inducible and ras-recision gene, TSC-36, in human cancer cells", *Cancer Letters.* 113(1-2): 213-219 (1997).

Massague et al., "Controlling TGF-beta signaling", *Genes Development.* 14(6):627-644 (2000).

Miyamae et al., "Follistatin-like protein-1 is a novel proinflammatory molecule", *J Immunol.* 177(7):4758-4762 (2006).

Miyamae et al., "682. Over-Expression of Follistatin-Like Protein Exacerbates Collagen Induced Arthritis", *Molecular Therapy,* 11:S264 (2005).

Molecular Cloning: A Laboratory Manual, Second Edition (Sambrook et al., 1989). Table of contents.

Molecular Cloning: A Laboratory Manual, Third Edition (Sambrook and Russel, 2001). Table of contents.

Moustakas, "Smad signalling network", *J. Cell Sci.* 115(Pt. 17):3355-3356 (2002).

Okabayashi et al., "cDNA cloning and distribution of the Xenopus follistatin-related protein", *Biochem Biophys Res Commun.* 254(1): 42-48 (1999).

Ohashi et al., "TSC-36 (follistatin-related polypeptide) gene expression in estrogen receptor positive osteoblastic cell line, CDO7F", *Calcif Tissue Int,* 61(5): 400-403 (1997).

PCR: The Polymerase Chain Reaction, (Mullis, et al., eds., 1994). Table of contents.

Shibanuma et al., "Cloning from a mouse osteoblastic cell line of a set of transforming-growth-factor-beta 1-regulated genes, one of which seems to encode a follistatin-related polypeptide", *Eur J Biochemn.* 217(1):13-19 (1993).

Shin et al., "7,12-Dimethylbenz(a)Anthracene Treatment of a *c-rel* Mouse Mammary Tumor Cell Line Induces Epithelial to Mesenchymal Transition via Activation of Nuclear Factor-κB", *Cancer Res.* 66(5):2570-2575 (2006).

Sowders et al., "Follistatin-like gene expression is upregulated in murine collagen induced arthritis", *FASEB Journal Fed. American Soc. For Experimental Biology,* 16(4):A326, (2002).

Sudo et al., "In vitro differentiation and calcification in a new clonal osteogenic cell line derived from newborn mouse calvaria", *J. Cell Biol.* 96(1):191-198 (1983).

Sumitomo et al., "Expression of TGF-β1 inducible gene, TSc-36, causes growth inhibition in human lung cancer cell lines", *Cancer Letters,* 155(1): 37-46 (2000).

Tanaka et al., "Cloning of follistatin-related protein as a novel autoantigen in systemic rheumatic diseases", *Int Immunol.* 10(9): 1305-1314 (1998).

Tanaka et al., "Potential preventive effects of follistatin-related proteinITSC-36 on joint destruction and antagonistic modulation of its autoantibodies in rheumatoid arthritis", *Int Immunol.* 15(1):71-77 (2003).

Thornton et al., "DNA micrbarray analysis reveals novel gene expression profiles in collagen-induced arthritis", *Clinical Immunology.* 105(2):155-168 (2002).

Thornton et al., "NK cells secrete high levels of IFN-gamma in response to in vivo administration of IL-2", *European Journal of Immunology.* 31(11):3355-3360 (2001).

Thornton et al., "Heterogeneous effects of IL-2 on collagen-induced arthritis", *J. Immunol.* 165(3):1557-1563 (2000).

Trojan et al., "Identification of metastasis-associated genes in prostate cancer by genetic profiling of human prostate cancer cell lines", *Anticancer Res.* 25(1A):183-191 (Jan.-Feb. 2005).

Yamada et al., "TNF:TNF-R T-Cell costimulatory pathways in transplantation", *Transplant Pnac.* 33(7-8):3070-3071 (2001).

van Stipdonk et al., "Dynamic programming cf CD8+ T lymphocyte responses", *Nat Immunol.* 4(4):361-365 (2003).

Wilson, et al. "Follistatin-like Protein 1 is a Mesenchyme-Derived Inflammatory Protein and May Represent a Biomarker for Systemic-onset Juvenile Rheumatoid Arthritis", *Arthritis & Rheumatism,* 62(8): 2510-2516 (2010).

* cited by examiner

FSTL-1 AS A BIOMAKER OF INFLAMMATION

CROSS-REFERENCE TO RELATED APPLICATIONS

This application is a 35 U.S.C. 371 National Phase of International Application PCT/US09/032429, filed Jan. 29, 2009, which claims priority to U.S. Provisional Application Ser. No. 61/024,487, filed on Jan. 29, 2008, the contents of each of which are hereby incorporated herein by reference in their entireties.

FIELD OF THE INVENTION

The invention provides for methods and kits of using levels of follistatin-like protein-1 (FSTL-1) as a biomarker to determine severity of inflammatory diseases, in particular, rheumatic diseases, and infectious diseases.

BACKGROUND OF THE INVENTION

Rheumatic diseases are characterized by inflammation (e.g., redness and/or heat, swelling, and pain) and loss of function of one or more connecting or supporting structures of the body. These types of diseases affect joints, tendons, ligaments, bones, and muscles. The most common symptoms include, but are not limited to, pain, swelling, and stiffness. Some rheumatic diseases can also involve internal organs. There are more than 100 rheumatic diseases.

Some of the more commonly known rheumatic diseases include juvenile rheumatic arthritis, Kawasaki disease and various forms of arthritis such as rheumatoid arthritis (RA) and osteoarthritis (OA). Juvenile rheumatoid arthritis (JRA) is the most common form of arthritis in childhood, causing pain, stiffness, swelling, and loss of function of the joints. Juvenile rheumatoid arthritis causes joint inflammation and stiffness for more than 6 weeks in a child of 16 years of age or less. The arthritis may be associated with rashes or fevers, and may affect various parts of the body. Rheumatologists classify JRA into three main types (pauciarticular, polyarticular, and systemic) depending on the number of joints involved, the symptoms and the presence or absence of certain antibodies found by a blood test.

Pauciarticular arthritis means that four or fewer joints are affected. Pauciarticular arthritis is the most common form of JRA—about half of all children with JRA have this type. Pauciarticular disease typically affects large joints, such as the knees. Girls under age 8 are most likely to develop this type of JRA.

Polyarticular arthritis means that five or more joints are affected. About 30 percent of all children with JRA have polyarticular disease. The small joints, such as those in the hands and feet, are most commonly involved, but the disease may also affect large joints. Polyarticular JRA often is symmetrical; that is, it affects the same joint on both sides of the body. Some children with polyarticular disease have an antibody in their blood called IgM rheumatoid factor (RF). These children often have a more severe form of the disease, which doctors consider to be similar in many ways to adult rheumatoid arthritis.

The most severe type of JRA is systemic arthritis. Besides joint swelling, the systemic form of JRA is characterized by fever and a light skin rash, and may also affect internal organs such as the heart, liver, spleen, and lymph nodes. Rheumatologists sometimes call it Still's disease. Almost all children with this type of JRA test negative for both RF and antinuclear antibody (ANA). The systemic form affects 20 percent of all children with JRA. A small percentage of these children develop arthritis in many joints and can have severe arthritis that continues into adulthood.

Diagnosis of JRA involves a combination of observation of symptoms and laboratory tests. Doctors usually suspect JRA, along with several other possible conditions, when they see children with persistent joint pain or swelling, unexplained skin rashes and fever, or swelling of lymph nodes or inflammation of internal organs. A diagnosis of JRA also is considered in children with an unexplained limp or excessive clumsiness. Currently, no single test or biomarker can be used to diagnose JRA and its disease severity. A doctor diagnoses JRA by carefully examining the patient and considering the patient's medical history, the results of laboratory tests, and x-rays that help rule out other conditions. Laboratory tests usually measure levels of ANA and erythrocyte sedimentation rate (ESR). However, these types of tests do not provide accurate correlations with disease severity. As such, there is a need for an accurate test to diagnose JRA and especially to determine the severity of JRA.

Kawasaki disease is another type of inflammatory disease that mostly affects children. Kawasaki disease is an illness that involves the skin, mouth, and lymph nodes, and typically affects children who are under the age of 5. The cause of Kawasaki disease is unknown, but if the symptoms are recognized early, children with the disease can fully recover within a few days. If it goes untreated, it can lead to serious complications that can involve the heart. Currently, the primary method of diagnosis of Kawasaki disease is observation of symptoms, which can include severe redness in the eyes; a rash on the child's stomach, chest, and genitals; red, dry, cracked lips; swollen tongue with a white coating and big red bumps; sore, irritated throat; swollen palms of the hands and soles of the feet with a purple-red color; and swollen lymph nodes. Accordingly, there is another need for a method of diagnosing this type of disease and its severity as well.

Adult rheumatic diseases occur in many forms. One common rheumatic disease is arthritis, of which there are many types. Common symptoms of arthritis include: swelling in one or more joints, stiffness around the joints that lasts for at least 1 hour in the early morning, constant or recurring pain or tenderness in a joint, difficulty using or moving a joint normally and warmth and redness in a joint. The most common type of arthritis is osteoarthritis. This type of arthritis affects an estimated 21 million adults in the United States. Osteoarthritis primarily affects cartilage, which is the tissue that cushions the ends of bones within the joint. In osteoarthritis, the cartilage begins to fray and may entirely wear away. Osteoarthritis can cause joint pain and stiffness. Disability results most often when the disease affects the spine and the weight-bearing joints (the knees and hips). Osteoarthritis is a type of non-erosive arthritis.

Yet another type of rheumatic disease is rheumatoid arthritis. This inflammatory disease of the synovium, or lining of the joint, results in pain, stiffness, swelling, joint damage, and loss of function of the joints. Inflammation most often affects joints of the hands and feet and tends to be symmetrical (occurring equally on both sides of the body). This symmetry helps distinguish rheumatoid arthritis from other forms of the disease. Rheumatoid arthritis is a type of erosive arthritis.

As with the juvenile rheumatic diseases, diagnosis of adult rheumatic diseases often involves a combination of observing symptoms and laboratory tests. Such laboratory tests include ANA, C-reactive protein (CRP), complete, complete blood count (CBC), creatinine, erythrocyte sedimentation rate (ESR), hematocrit, RF, urinanalysis, white blood cell count, and x-ray. However, there is no single diagnostic biomarker that can determine the disease severity of rheumatic diseases. Accordingly, there exists a great need for a type of marker that can not only diagnose the existence of a particular inflammatory or rheumatic disease state, but also assess the severity of the disease. Such a diagnostic marker would be very helpful for creating a treatment plan for an individual suffering from such diseases and also be useful to track prognosis following the initiation of a treatment plan.

The invention provided herein addresses these needs by disclosing, inter alia, methods and kits for using a single biomarker, follistatin-like protein-1 (FSTL-1), to assess disease states and/or severity of various inflammatory diseases, including rheumatic diseases.

Follistatin-Like Protein-1 (FSTL-1)

FSTL-1 (also known as FRP or TSC-36) is an extracellular glycoprotein belonging to the BM-40/SPARC/osteonectin family of proteins containing both extracellular calcium-binding and follistatin-like domains. See e.g., U.S. Pat. No. 6,410,232. FSTL-1 was originally cloned from an osteoblastic cell line as a TGF-β inducible gene. M. Shibanuma et al., *Eur J Biochem* 217, 13 (1993). The protein occurs in two isoforms resulting from differential sialylation. FSTL-1 has been detected in the medium of all osteosarcoma and chondrosarcoma cell lines, and in some cells of the fibroblast lineage. In mice, the highest expression of FSTL-1 has been observed in the lung. J. Mashimo et al., *Cancer Lett* 113, 213 (1997).

The action of FSTL-1 is unclear, and both proliferative and anti-proliferative effects have been reported. It is thought that FRP may play a role in neuralization during embryogenesis and its expression is upregulated by estrogen. See K. Okabayashi et al., *Biochem Biophys Res Commun* 254, 42 (Jan. 8, 1999) and T. Ohashi et al., *Calcif Tissue Int* 61, 400 (November, 1997). In contrast to other BM-40 family members, the extracellular calcium-binding domain of FSTL-1 is non-functional, suggesting that, despite its sequence homology to BM-40, it has evolved clearly distinct properties. H. O. Hambrock et al., *Journal of Biological Chemistry* 279, 11727 (Mar. 19, 2004). Analysis of prostate cancers has revealed that over-expression of FSTL-1 may be associated with higher metastatic potential. L. Trojan et al., *Anticancer Res* 25, 183 (January-February, 2005). In contrast, FSTL-1 expression has been extinguished in v-ras-transformed rat fibroblasts, and transfection of FSTL-1 into these cells inhibited in vitro invasion and led to growth inhibition in human lung cancer cells. See I. M. Johnston et al., *Oncogene* 19, 5348 (Nov. 9, 2000) and K. Sumitomo et al., *Cancer Lett* 155, 37 (Jul. 3, 2000).

In addition, it has previously been shown that FSTL-1 is highly-upregulated in the joints during the acute phase of collagen-induced arthritis (CIA), most prominently at the junction of synovium and eroding bone, suggesting a role in joint destruction. S. Thornton et al., *Clin Immunol* 105, 155 (2002).

In 1998, Tanaka et al. cloned FRP from rheumatoid arthritis (RA) synovial tissue and demonstrated the presence of anti-FSTL-1 antibodies in the serum and synovial fluid of RA patients. M. Tanaka et al., *International Immunology* 10, 1305 (1998). In addition, Tanaka et al. analyzed the mRNA expression and protein expression of FRP in from patients with RA and patients with osteoarthritis (OA) and found that the FRP mRNA expression was higher in RA than in OA synovial samples. Importantly, Tanaka et al. concluded that there was no difference in the protein levels of FRP between these two groups.

Ehara et al. measured mRNA expression of FRP in synovial fluid from patients with RA and patients with OA. They found the mRNA expression of FRP was 2.3 fold higher in the RA patients than in the OA patients. Y. Ehara et al., *Clin Exp Rheumatol* 22, 707 (2004). Importantly, the authors stated that the FRP may exert a protective effect for joint destruction on synoviocytes.

Other groups have used mass spectroscopy to characterize the expression of a large number of genes to determine whether one or a combination of genes could be used for diagnostic purposes. For example, in WO 2005/032328, over 500 genes are disclosed as part of a mass screening. One of these genes (M285 in Table 1) is FSTL-1. Importantly, the data shows that the levels of FSTL-1 protein decreases in patients with erosive arthritis and also in patients with non-erosive arthritis as compared to healthy (normal) individuals (i.e., without arthritis).

Another publication, WO 2004/0018522 describes measurement of mRNA expression levels for a large number of genes to diagnose or predict multiple sclerosis. FSTL-1 appears in Table 3 and 9, however, only mRNA levels are measured and there is very limited disclosure that connects such expression in multiple sclerosis patients with arthritis (or, by extension, to other rheumatic diseases).

Finally, Miyamae et al. reported that FSTL-1 was a novel pro-inflammatory molecule with an unrecognized role in inflammation. T. Miyamae et al. *J. Immunol.* 177, 4758 (2006). Importantly, there was no disclosure in this reference that teaches or even suggests using protein levels of FSTL-1 as a biomarker for assessing disease severity in inflammatory diseases. As such, the invention describes a novel diagnostic biomarker that is capable of assessing disease severity in inflammatory and/or rheumatic diseases.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provides methods of diagnosing severity of disease states for various inflammatory and rheumatic diseases by assessing the protein levels of follistatin-like protein-1 (FSTL-1). In one aspect, the invention provides a method of assessing the severity of an inflammatory disease in an individual by assessing the level of protein expression of FSTL-1 in a biological sample from the individual and correlating the level of protein expression of FSTL-1 with the severity of the disease wherein a higher level of FSTL-1 expression relative to a normal individual is associated with a greater severity of the disease. Examples of inflammatory diseases include juvenile rheumatoid arthritis, Kawasaki's disease, rheumatoid arthritis, gouty arthritis, psoriatic arthritis, septic arthritis, osteoarthritis, and reactive arthritis. Juvenile rheumatoid arthritis can be subclassified based on the severity of the disease; the most severe form of juvenile rheumatoid arthritis is systemic juvenile rheumatoid arthritis, the less severe form of juvenile rheumatoid arthritis is polyarticular juvenile rheumatoid arthritis, and the least severe form of juvenile rheumatoid arthritis is pauciarticular juvenile rheumatoid arthritis. Examples of biological samples of the invention include plasma, serum, synovial fluid, broncheoalveolar lavage fluid, cerebrospinal fluid, pleural fluid and pericardial fluid.

In another aspect, the invention provides a method for assessing the degree of erosiveness of arthritis in an individual by assessing the level of protein expression of FSTL-1 in a biological sample from the individual and correlating the level of expression of FSTL-1 with the severity of the disease wherein a higher level of FSTL-1 expression relative to a normal individual is associated with erosive arthritis. The highest level of FSTL-1 is predictive of erosive disease, a moderate level of FSTL-1 is predictive of moderately erosive disease and a low level of FSTL-1 is predictive of non-erosive disease.

In another aspect of the invention, the level of FSTL-1 is assessed prior to the start of a treatment plan and monitored during the course of treatment to determine the efficacy of the treatment plan.

The invention also provides a method of assessing infectious disease in an individual by assessing the level of protein expression of FSTL-1 in a biological sample from the individual relative to a normal individual. Examples of infectious disease include bacterial infection, viral infection and septic shock.

SEQUENCE LISTING

Figure 1:
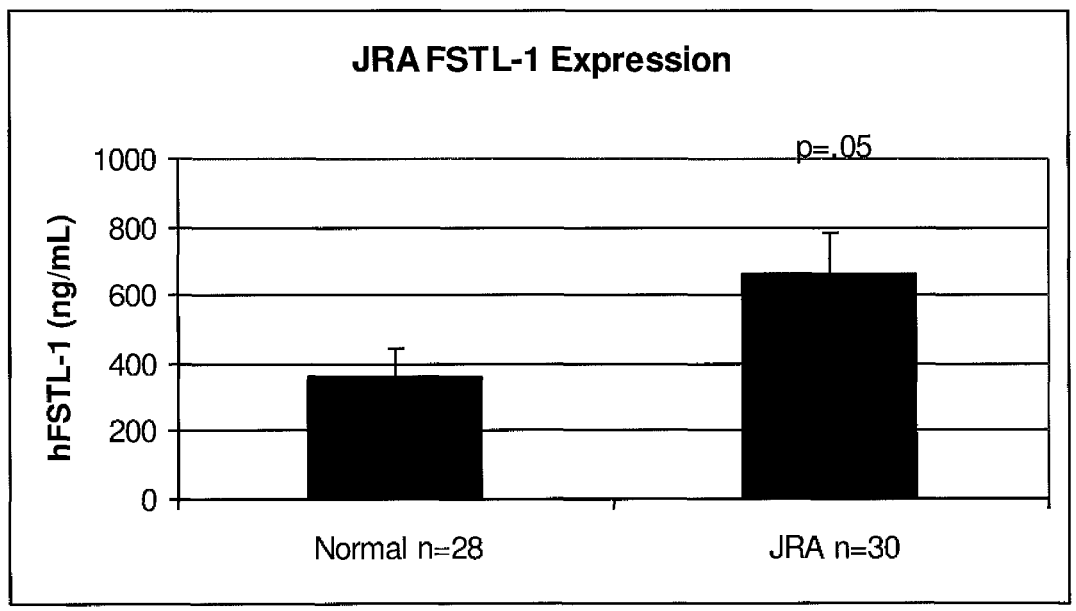
FIG. 1 shows FSTL-1 serum levels in children with JRA and normal children without JRA.

The specification further incorporates by reference the Sequence Listing submitted herewith via EFS on Nov. 1, 2010. Pursuant to 37 C.F.R. §1.52(e)(5), the Sequence Listing text file, identified as 0723960412.txt, is 2.61 kilobytes and was created on Nov. 1, 2010. The Sequence Listing, electronically filed herewith, does not extend beyond the scope of the specification and thus does not contain new matter.

DETAILED DESCRIPTION OF THE INVENTION

The invention provides methods and kits for diagnosing disease severity of rheumatic and infectious diseases by measuring protein levels of follistatin-like protein-1 (FSTL-1). The invention is useful for determining the disease states of various types of rheumatic and infectious diseases so that appropriate treatment plans can be determined. The invention is also useful to following disease severity after the implementation of any treatment plans.
General Techniques The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., and *Current Protocols in Nucleic Acid Chemistry* John Wiley & Sons, Inc., New York, 2000).

DEFINITIONS

The term "sample", as used herein, refers to a composition that is obtained or derived from an individual that contains a cellular and/or other molecular entity that is to be characterized and/or identified, for example based on physical, biochemical, chemical and/or physiological characteristics. In one embodiment, the sample is taken from the serum. In another embodiment, the sample is taken from synovial fluid.

An "individual" is a vertebrate, such as mouse, and is preferably a mammal, more preferably a human. Mammals include, but are not limited to, humans, primates, farm animals, sport animals, rodents and pets.

A "patient" refers to an "individual" who is under the care of a treating physician. Patients can be of varying ages. In one embodiment, patients are humans. In another embodiment, patients are human children. In another embodiment, patients are human adults.

As used herein, "array" and "microarray" are interchangeable and refer to an arrangement of a collection of nucleotide sequences or proteins (and/or agents for detecting target protein(s)) in a centralized location. Arrays can be on a solid substrate, such as a glass slide, or on a semi-solid substrate, such as nitrocellulose membrane. The nucleotide sequences can be DNA, RNA, or any permutations thereof The nucleotide sequences can also be partial sequences from a gene, primers, whole gene sequences, non-coding sequences, coding sequences, published sequences, known sequences, or novel sequences. In one embodiment, a protein array comprises FSTL-1. In another embodiment, the level of FSTL-1 protein can be determined using levels of mRNA of FSTL-1.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, refers to short, single stranded polynucleotides that are at least about seven nucleotides in length and less than about 250 nucleotides in length. Oligonucleotides may be synthetic. The terms "oligonucleotide" and "polynucleotide" are not mutually exclusive. The description above for polynucleotides is equally and fully applicable to oligonucleotides.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. In another example, one may use the results of a first analysis of a first individual (or patient) suspected of having a type of inflammatory disease and comparing with the results of a second analysis of a second individual who is known to not have such inflammatory disease (or alternatively, a standard) for correlation to determine the severity of the inflammatory disease in the first individual. With respect to the embodiment of FSTL-1 analysis or protocol, one may use the results of the FSTL-1 analysis or protocol to determine whether a specific therapeutic regimen should be performed depending on the severity of the disease and/or type of disease.

The term "diagnosis" is used herein to refer to the identification or classification of a molecular or pathological state, disease or condition. For example, "diagnosis" may refer to identification of a particular type of inflammatory disease, e.g., rheumatoid disease. "Diagnosis" may also refer to the classification of a particular sub-type of rheumatoid disease, such as rheumatoid arthritis. In one embodiment, "diagnosis" may also refer to the level of severity of a disease.

The term "aiding diagnosis" is used herein to refer to methods that assist in making a clinical determination regarding the presence, degree or other nature, of a particular type of symptom or condition of inflammatory disease. For example, a method of aiding diagnosis of inflammatory disease can comprise measuring the amount or detecting the level of FSTL-1 in a biological sample from an individual. In another example, a method of aiding diagnosis of inflammatory disease can comprise measuring the amount or detecting the presence of FSTL-1 in a biological sample from an individual.

The term "prognosis" is used herein to refer to the prediction of the progression of various types of inflammatory disease, including rheumatic and infectious diseases. Diseases that are contemplated include, but are not limited to, osteoarthritis (OA), rheumatoid arthritis (RA), juvenile rheumatoid arthritis (JRA), Kawasaki disease, fibromyalgia, systemic lupus erythematosus, scleroderma, spondyloarthropathies, gout, infectious arthritis, polymyalgia rheumatica, polymyo-sitis, psoriatic arthritis, bursitis, tendonitis, bacterial infection, viral infection and septic shock. The methods of the invention can be used clinically to make treatment decisions by choosing the most appropriate treatment modalities for any particular patient. The methods of the present invention are valuable tools in diagnosing and/or aiding in the diagnosis as to the severity of the disease, which may factor into the prognosis of the disease. Treatments can be prescribed for the patient based on the prognosis. Prognosis of the diseases above may be made according to any protocol that one of skill of art would use, for example, those set by the American College of Rheumatology.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "medicament" is an active drug to treat a disease, disorder, and/or condition. In one embodiment, the disease, disorder, and/or condition is rheumatoid arthritis or its symptoms or side effects associated with treatment of rheumatoid arthritis.

Reference to "about" a value or parameter herein includes (and describes) embodiments that are directed to that value or parameter per se. For example, description referring to "about X" includes description of "X."

It is understood that aspect and embodiments of the invention described herein include "consisting" and/or "consisting essentially of" aspects and embodiments.

Methods for Diagnosis

The invention provides for methods of using the protein expression of a single biomarker, FSTL-1, to determine the disease severity of various types of inflammatory diseases, including rheumatic and infectious diseases. Diseases that are contemplated include, but are not limited to, osteoarthritis (OA), rheumatoid arthritis (RA), juvenile rheumatoid arthritis (JRA), Kawasaki disease, fibromyalgia, systemic lupus erythematosus, scleroderma, spondyloarthropathies, gout, infectious arthritis, polymyalgia rheumatica, polymyositis, psoriatic arthritis, bursitis, tendonitis, bacterial infection, viral infection and septic shock.

FSTL-1 is used as a biomarker by assessing the protein levels of FSTL-1 in a biological sample from an individual. The biological sample includes, but is not limited to, cells (e.g., peripheral blood mononuclear cells (PBMC), plasma, serum, synovial fluid, broncheoalveolar lavage fluid, cerebrospinal fluid, pleural fluid and pericardial fluid. In one aspect of the invention, the assessment of expression is at the protein levels and not at the mRNA or nucleic acid level. In another aspect of the invention, the assessment of expression is at the nucleic acid levels (e.g., mRNA levels). Care should be taken to make sure that mRNA does not degrade so that accurate levels can be measured. It is to be understood that measurement of nucleic acid levels (e.g., mRNA levels) can be used as a surrogate or in place of protein levels throughout the specification.

The assessment of protein levels is routine and known to one of skill in the art. One possible method of measuring protein levels is by using immunoprecipitation (using commercially available antibodies to FSTL-1/FRP/TSC-36) followed by Western blotting. However, sensitivity of the protein assay is important since there is a direct correlation between the level of FSTL-1 protein and the severity of the disease state. As such, ELISA or other more sensitive methods of measuring FSTL-1 protein expression is recommended. As an example of this, the protein levels of FRP (same as FSTL-1) were found to be virtually non-existent in plasma of normal individuals by Taneka et al. by using IP/Western blotting techniques. In contrast, the inventors have found that individuals without RA (e.g., normal individuals) still express FSTL-1 but at a statistically significantly less amount than those individuals with RA.

The protein levels of FSTL-1 are measured in the individual to be tested for one or more inflammatory or rheumatic disease and compared to those levels in normal individuals. By "normal individuals," these are individuals who do not have the inflammatory or rheumatic disease that is being tested. In another aspect of the invention, the FSTL-1 levels from an individual to be tested is compared to an individual without any inflammatory or rheumatic diseases and is diagnostic or aids in the diagnosis of the severity of such diseases if there is 25% increase when compared the individual without any inflammatory or rheumatic diseases. In other embodiments, the FSTL-1 levels from an individual to be tested is compared to an individual without any inflammatory or rheumatic diseases and is diagnostic or aids in the diagnosis of the severity of such diseases if there is 30%, 35%, 40%, 45%, 50%, 55%, 60%, 65%, 70%, 75%, 80%, 85%, 90%, 95%, 100%, 125%, 150%, 200%, 250%, 300%, 350%, 400%, 450%, 500%, 550%, or 600% increase in FSTL-1 levels when compared the individual without any inflammatory or rheumatic diseases.

Alternatively, bacterially purified FSTL-1 (or any other organism capable of expressing FSTL-1 including insect cells infected with recombinant baculovirus expressing FSTL-1) can also be used as a standard. In one aspect, the overexpression of FSTL-1 protein relative to normal individuals is predictive for that individual having at least one form of inflammatory disease. In some embodiments, the inflammatory disease is also a rheumatic disease. FIG. 1 illustrates that children with JRA have a statistically significantly higher level of FSTL-1 protein expression as compared to normal children (i.e., children who do not have JRA).

In another aspect, the protein levels of FSTL-1 has a direct (i.e., not inverse) correlation with the severity of the disease state. In one embodiment, the children with the highest level of FSTL-1 have the most severe form of JRA, systemic rheumatoid arthritis. See, for example, FIG. 2. The levels of FSTL-1 protein expression that are predictive for systemic rheumatoid arthritis are generally about 800 ng/ml and higher. In another aspect, children with moderate levels of FSTL-1 protein expression have less severe forms of JRA, such as pauciarticular arthritis and polyarticular arthritis. Moderate levels of FSTL-1 are generally about 500 ng/ml to about 800 ng/ml. In contrast, normal children (i.e., children who do not have JRA) have FSTL-1 levels that are about 400 ng/ml or lower. In other aspects of the invention, the levels of FSTL-1 protein expression that are predictive for systemic rheumatoid arthritis are generally at least about 800 ng/ml and higher. In another aspect, children with moderate levels of FSTL-1 protein expression have less severe forms of JRA, such as pauciarticular arthritis and polyarticular arthritis. Moderate levels of FSTL-1 are generally at least about 500 ng/ml to at least about 800 ng/ml. In contrast, normal children (i.e., children who do not have JRA) have FSTL-1 levels that are at least about 400 ng/ml or lower.

In another aspect of the invention, the level of FSTL-1 to be used for diagnosis or aiding in the diagnosis is in the picogram to nanogram range. In one embodiment, the level of FSTL-1 to be used for diagnosis or aiding in the diagnosis is in the low nanogram range (e.g., 1, 2, 3, et seq. ng). In one embodiment, the level of FSTL to be used for diagnosis or aiding in the diagnosis is from at least about 1 pg to at least about 100 ng. In other embodiments, the level of FSTL to be used for diagnosis or aiding in the diagnosis is from at least about 1 pg to at least about 100 ng, at least about 5 pg to at least about 75 ng, at least about 10 ng to at least about 50 ng, at least about 25 pg to at least about 25 ng, at least about 50 pg to at least about 10 ng, at least about 100 pg to at least about 10 ng, at least about 200 pg to at least about 5 ng, or at least about 300 pg to at least about 1 ng.

Figure 3:
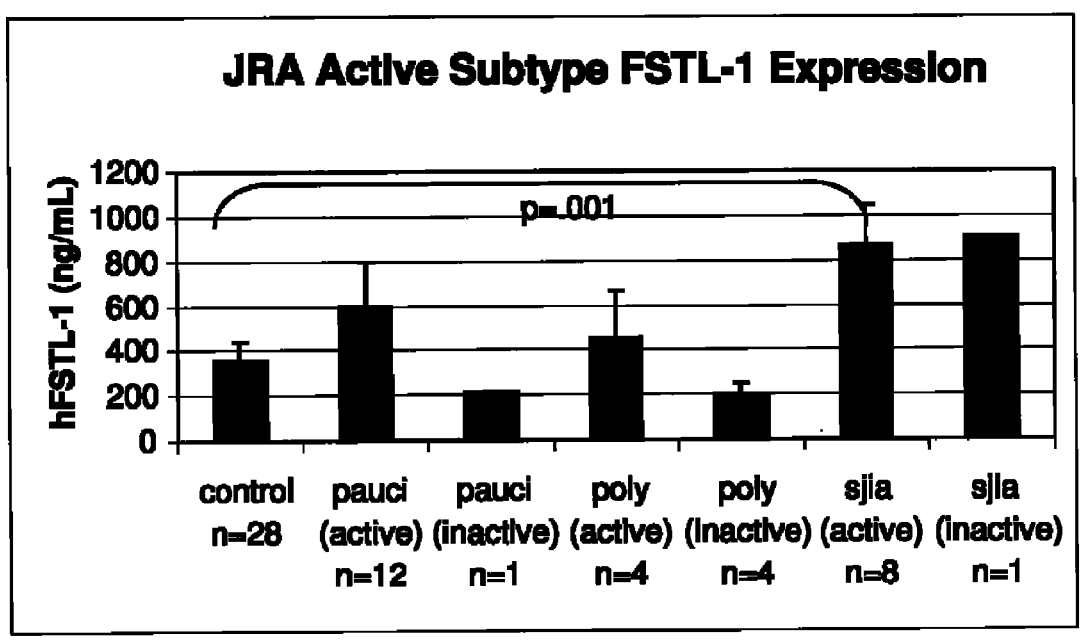
FIG. 3 shows the level of FSTL-1 in children with either active or inactive forms of pauciarticular arthritis, polyarticular arthritis, or systemic JRA.

Further, lower FSTL-1 levels are also observed in the sera from children with inactive forms of the less severe types of JRA. As used here, "active" and "inactive" states refer to the presence or absence, respectfully, of the common symptoms listed above. For example, as shown in FIG. 3, inactive forms of pauciarticular arthritis and polyarticular arthritis have levels of FSTL-1 protein expression that is similar to that of normal (control) children. In contrast, high levels (greater than about 800 ng/ml) of FSTL-1 protein are seen in the most severe form of JRA, systemic rheumatoid arthritis, regardless of whether the systemic JRA was active or inactive. Accordingly, one of skill in the art, such a physician, can use FSTL-1 as a biomarker for the status (active or inactive) when diagnosing children with the less severe forms of JRA. When used as a biomarker for systemic JRA, elevated levels of FSTL-1 are consistently observed regardless of whether the disease is active or inactive. Additionally, FSTL-1 is also useful as biomarker for assessing active states of JRA as part of monitoring the progress of JRA in the course of a treatment plan.

Figure 4:
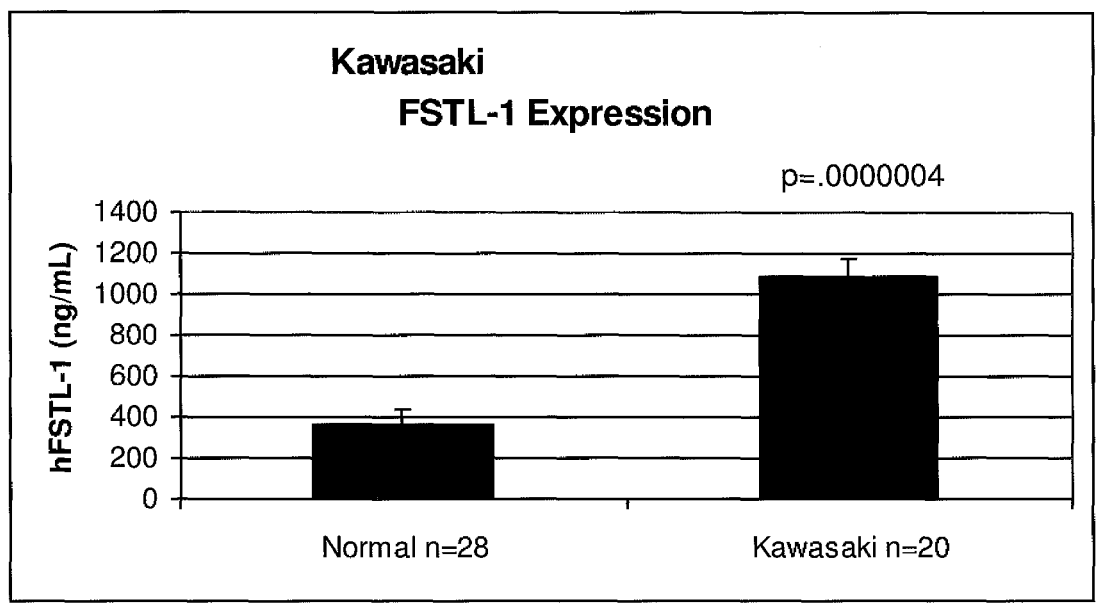
FIG. 4 shows FSTL-1 serum levels in Japanese children with Kawasaki disease and normal children without Kawasaki disease.

In another aspect of the invention, elevated levels of FSTL-1 is also a biomarker for Kawasaki disease. As shown in FIG. 4, children with Kawasaki disease have a highly statistically significant overexpression of FSTL-1 as compared to normal children (children without Kawasaki disease). As such, FSTL-1 can also be used to diagnose individuals with Kawasaki disease. The invention also provides for methods of assessing the severity of rheumatic disease in adults. The protein levels of FSTL-1 are predictive of the severity of erosion in arthritic diseases. In one embodiment, the level of FSTL-1 in synovial fluids in individuals with a non-erosive form of arthritis, such as osteoarthritis (OA), is about 500 ng/ml or less, very similar levels to that of normal individuals. The level of FSTL-1 in individuals with an erosive form of arthritis, such as rheumatoid arthritis (RA), tends to be in the thousand or thousands of FSTL-1 (ng/ml). Accordingly, one of skill in the art can diagnose an individual's disease severity by using the level of FSTL-1 protein expression. Very high levels of FSTL-1 protein expression would indicate a severe form of rheumatic disease, such as erosive arthritis or systemic forms of arthritis. Lesser amounts of FSTL-1 expression would indicate a milder form of arthritis, such as gout or reactive arthritis.

In another aspect of the invention, the biological sample that is used for measuring protein expression of FSTL-1 is either serum or synovial fluid. In one embodiment, serum is the preferred biological sample for measuring FSTL-1 levels. When using a sensitive protein assay, as indicated above, the diagnostic and/or predictive capabilities of FSTL-1 levels do not differ between serum and synovial fluid. In one embodiment, serum yields results that are equally reliable, if not better, than synovial fluids. Additionally, for the patient's convenience, serum is easier to obtain and less intrusive and less painful than synovial fluid. Accordingly, in one preferred embodiment of the invention, serum is used to measure FSTL-1 levels and then correlated with the severity of a disease state.

The methods of this invention are also used to monitor the progression of a treatment plan. FSTL-1 protein levels are assessed prior the start of any treatment program. This allows one of skill in the art, e.g., a physician, to assess the severity of the disease and to make recommendations for treatment plans. Once the treatment plan starts, FSTL-1 levels are continually monitored, for example by testing the individual's serum, to determine if the disease is progressing to a more severe state. In such manner, one can determine if the treatment plan is effective and if not, utilize a different treatment plan.

The individual that is determining the level of FSTL-1 does not necessarily have to be the same person who makes the diagnosis. For example, the invention contemplates situations when physicians take a biological sample from their patients, send the biological sample to another party to determine the FSTL-1 levels, receive the information about the FSTL-1 level and makes the diagnosis for their patient.

The methods of this invention are also used to monitor the progression of a treatment plan for infectious disease. FSTL-1 protein levels are assessed prior the start of any treatment program. Once the treatment plan starts, FSTL-1 levels are continually monitored, for example by testing the individual's serum, to determine if the individual is responding to the treatment. In such manner, one can determine if the treatment plan is effective and if not, utilize a different treatment plan.

Arrays

Arrays and microarrays which comprise FSTL-1 are described herein for assessing the severity of inflammatory diseases, including rheumatic and infectious diseases. Diseases that are contemplated for diagnostic purposes include, but are not limited to, osteoarthritis (OA), rheumatoid arthritis (RA), juvenile rheumatoid arthritis (JRA), Kawasaki disease, fibromyalgia, systemic lupus erythematosus, scleroderma, spondyloarthropathies, gout, infectious arthritis, polymyalgia rheumatica, polymyositis, psoriatic arthritis, bursitis, tendonitis, bacterial infection, viral infection and septic shock are also encompassed within the scope of this invention. Methods of making arrays are well-known in the art and as such, do not need to be described in detail here.

Protein arrays are well-known to those in the art. Various types of protein arrays (e.g., analytical microarrays, functional microarrays, and reverse phase microarrays) may be used to detect levels of FSTL-1 protein. Accordingly, in one aspect of the invention, a protein array comprising agents, such as capture agents (e.g., antibodies, aptamers, affibodies, peptides, full-length functional proteins or protein domains, tissue lysates for reverse phase microarrays), that bind to and/or interact with FSTL-1 is used as a diagnostic. Protein arrays may be used to detect FSTL-1 in combination with other proteins of interest (e.g., IL-1β, IFN-γ, TNF-α, IL-6, etc.) on the same array, which may be useful for diagnostic purposes in the context of inflammatory diseases.

In another embodiment, the array is an array probe of nucleic acids, such as a DNA chip, in which FSTL-1 is represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470, 710; 5,492,806; 5,503,980; 5,510,270; 5,525,464; 5,547,839; 5,580,732; 5,661,028; 5,800,992; WO 95/21265; WO 96/31622; WO 97/10365; WO 97/27317; EP 373 203; and EP 785 280.

Kits of the Invention

The invention provides composition comprising the reagents and/or materials needed to measure FSTL-1 levels in a biological sample. In one embodiment, bacterially purified FSTL-1 is provided as a standard in the kit. In another embodiment, FSTL-1 is purified from insect cells in which a recombinant baculovirus expressing FSTL-1 had been introduced. Instructions for conducting the determination of FSTL-1 protein levels are optionally included. In another embodiment, instructions for how to correlate the levels of FSTL-1 protein with disease severity are optionally included.

In another embodiment, the invention provides for kits comprising an array which comprises FSTL-1. As discussed infra, the array may be a protein array or a surrogate for detecting protein level (e.g., nucleic acid array). The kits of the subject invention may include the above described arrays. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g., hybridization and washing buffers, prefabricated probe arrays, labeled probe purification reagents and components, like spin columns, etc., signal generation and detection reagents, e.g., streptavidin-alkaline phosphatase conjugate, chemifluorescent or chemiluminescent substrate, and the like.

In addition to the above components, the kits will further include instructions for practicing the methods and arrays described herein. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Also provided are reagents and kits thereof for practicing one or more of the above described methods. The subject reagents and kits thereof may vary greatly. Reagents of interest include reagents specifically designed for use in production of the above described FSTL-1 protein.

Computer Readable Media Comprising FSTL-1

The invention also contemplates computer readable media that comprises information on FSTL-1. Such media can contain all of part of the data for levels of FSTL-1 and other medical information that would be helping in diagnosing or aiding in the diagnosis of inflammatory diseases as described herein.

Program Products/Systems

Another aspect of the invention provides a program product (i.e., software product) for use in a computer device that executes program instructions recorded in a computer-readable medium to perform statistical calculations relating to FSTL-1 levels for diagnostic purposes.

In one embodiment, the program product comprises: a recordable medium; and a plurality of computer-readable instructions executable by the computer device to analyze data from the array hybridization steps, to transmit array hybridization from one location to another, or to evaluate genome-wide location data between two or more genomes. Computer readable media include, but are not limited to, CD-ROM disks (CD-R, CD-RW), DVD-RAM disks, DVD-RW disks, floppy disks and magnetic tape.

A related aspect of the invention provides kits comprising the program products described herein. The kits may also optionally contain paper and/or computer-readable format instructions and/or information, such as, but not limited to, information on protein or nucleic acid microarrays, on tutorials, on experimental procedures, on reagents, on related products, on available experimental data, on using kits, on agents for treating inflammatory diseases, including their toxicity, and on other information. The kits optionally also contain in paper and/or computer-readable format information on minimum hardware requirements and instructions for running and/or installing the software.

It will be apparent to those of ordinary skill in the art that methods involved in the present invention may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, having a computer readable program code stored thereon.

The following examples are given to illustrate aspects of the invention. They are not meant to limit the invention in any manner.

EXAMPLES

Example 1

Assessing FSTL-1 Protein Levels

Assessing the protein levels of either mouse FSTL-1 (mFSTL-1) or human FSTL-1 (hFSTL-1) by ELISA was accomplished using the following materials and methods:

Solutions: Coating Buffer—PBS pH 7.4; Blocking Buffer—PBS with 1% BSA, 5% sucrose, and 0.05% Tween 20; Diluent—TBS pH 7.3 (20 nM Tris, 150 mM NaCl) with 0.1% BSA, 0.05% Tween 20; and Wash Buffer—PBS 0.05%, Tween-20.

Plate: Catalog #468667 or 434797 from Nunc Immunomodule, MaxiSorp™ F8 framed.

1. Coating→Coat the plate with 2 µg/ml of polyclonal goat anti-human FSTL-1 at 100 µl/well (R&D #AF 1694=0.1 mg/ml) or polyclonal goat anti-mouse FSTL-1 (R&D #AF 1738) at 4° C. overnight (20 µl+1 ml of PBS).

2. Wash three times with Wash Buffer.

3. Block the plate with 300 µl/well of blocking buffer at least 1 hour at room temperature.

4. Wash three times with Wash Buffer.

5. Sample loading→Load samples or bacterially purified human FSTL-1 100 µl/well (diluted with Diluent Buffer) in duplicate and incubate overnight at 4° C. The standard used for hFSTL-1 was bacterially purified hFSTL-1 at 10000 ng/mL (490 µl dil. buffer+10 µL standard=200 ng/ml). For mFSTL-1, bacterially purified mFSTL-1 at 10000 ng/mL (490 µl dil. buffer+10 µL standard=200 ng/ml) was used. A method to produce FSTL-1 in bacteria is provided in Example 7.

6. Wash plate three times.

7. Add 100 µl of first monoclonal rat anti-FSTL-1 mAb 1.25 µg/ml incubate for 1 hr at RT (20-25° C.) (R&D cat #MAB 1738, 500 µg/ml). Dilute 1:400 to a final concentration of 1.25 µg/ml.

8. Wash three times with Wash Buffer.

9. Add 100 µl of second polyclonal goat anti rat-HRP (KPL #04-16-02; 0.1 mg/ml; at 4° C., Box #12) incubate for 1 hr. at room temperature (20-25° C.). Diluted 1:500; final concentration will be 0.2 µg/ml.

10. Wash three times with Wash Buffer.

11. Substrate; ABTS mixture same dose of ARTS (A) and (B) less than 20 minutes before using and add 100 µl/well of mixed substrate.

12. Do OD reading at 405 nm to determine absorbance.

Example 2

Assessing Disease Severity for Juvenile Rheumatoid Arthritis (JRA)

Figure 2:
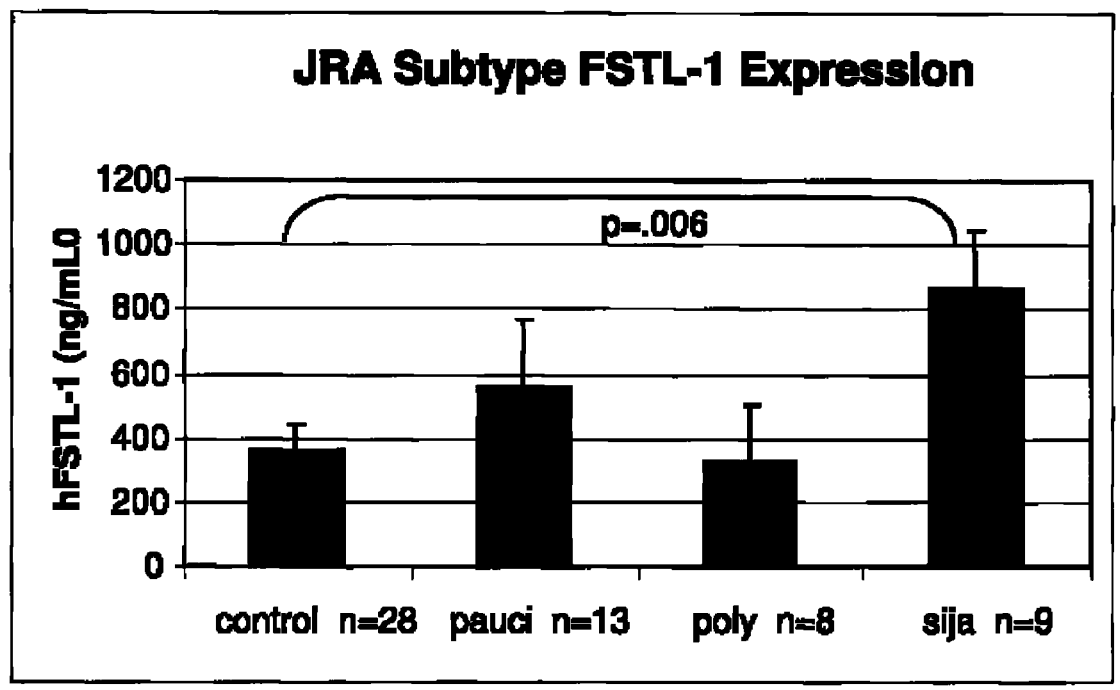
FIG. 2 shows the level of FSTL-1 in children with the three forms of JRA, pauciarticular arthritis, polyarticular arthritis, and systemic JRA.

The serum from children either with or without JRA were analyzed to determine the correlation between FSTL-1 protein levels and disease severity. Using the protocol above, FSTL-1 protein levels were determined for 28 normal children (i.e., children without JRA) and 31 children with JRA. As shown in FIG. 1, FSTL-1 levels were significantly higher (p=0.5) than in the normal children. The mean level of FSTL-1 protein for children with JRA was about 650 ng/ml and for normal children, it was below about 400 ng/ml. As a biomarker for disease severity, the expression of FSTL-1 was significantly higher (p=0.006) in children with systemic rheumatoid arthritis. This is shown in FIG. 2 where the mean levels of FSTL-1 expression were more than about 800 ng/ml for children with the most severe form of JRA. In contrast, children with the less severe forms of JRA, pauciarticular arthritis and polyarticular arthritis, expressed moderate to low levels of FSTL-1 as compared to normal children.

Example 3

FSTL-1 as a Biomarker for Active States of JRA

The sera from 28 normal children and from children with different forms of JRA in active or inactive states were analyzed for levels of FSTL-1 using the protocol described in Example 1. The results are shown in FIG. 3. The highest levels (e.g., >800 ng/ml) were seen in the children with the most severe form of JRA, regardless of whether the JRA was active or inactive (as defined by the presence or absence of symptoms, respectfully). In contrast, the status of pauciarticular arthritis and polyarticular arthritis was reflected in the levels of FSTL-1 detected. The sera from children with the active form of both types of JRA contained moderate levels of FSTL-1 whereas the serum from children with inactive form of pauciarticular arthritis and polyarticular arthritis were low, about the same level as normal children.

Example 4

FSTL-1 as a Biomarker for Kawasaki Disease

Sera were taken from 20 children with Kawasaki disease and analyzed for FSTL-1 levels. As a comparison, sera were also taken from 28 normal children (i.e., without Kawasaki disease). The children with the Kawasaki disease displayed a statistically significant higher level of FSTL-1 than normal children. For the children with Kawasaki disease, the mean was greater than 1000 ng/ml while for the normal children, the mean expression was less than 400 ng/ml.

Example 5

Induction of FSTL-1 Levels in a Mouse Model of Infection

Figure 5:
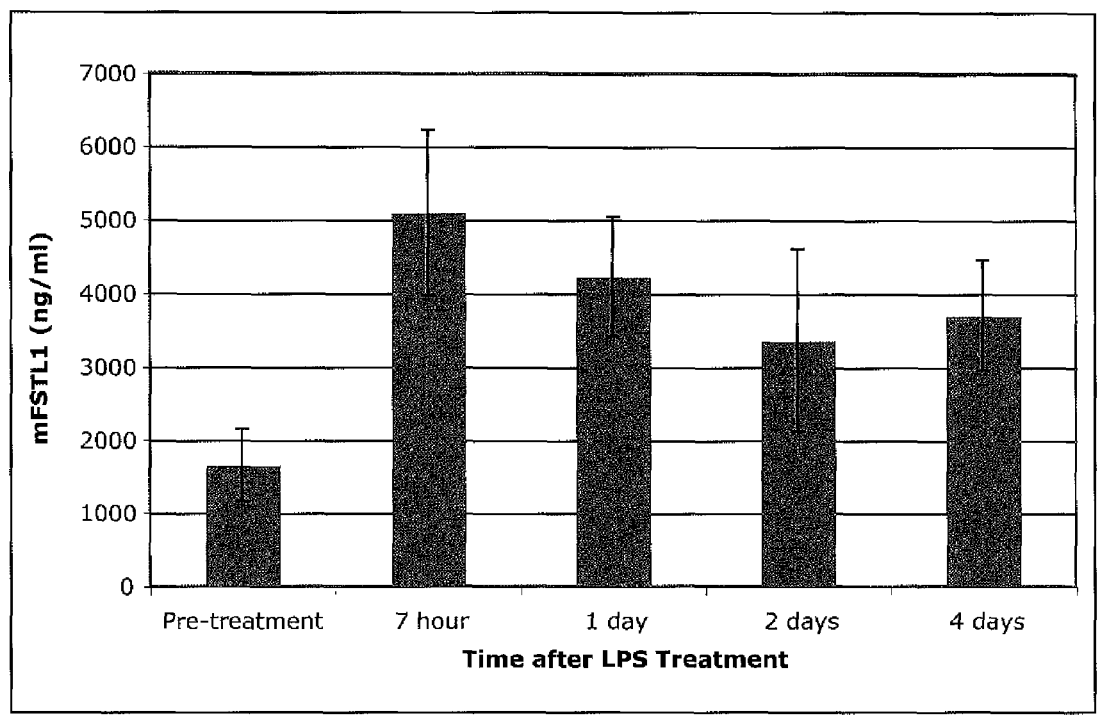
FIG. 5 shows FSTL-1 serum levels after I.P. injection of 50 micrograms LPS in mice.

LPS was administered to mice to mimic bacterial infection. Mice were given LPS and their sera were taken at certain intervals after the administration of LPS. As shown in FIG. 5, the mice showed elevated FSTL-1 levels in response to the LPS. The elevation of FSTL-1 was not seen in normal mice. Thus, this example showed that in an animal model of infection, FSTL-1 could serve as a biomarker for inflammation.

Example 6

Induction of FSTL-1 Levels in the Lungs in a Mouse Model of Infection

Figure 6:
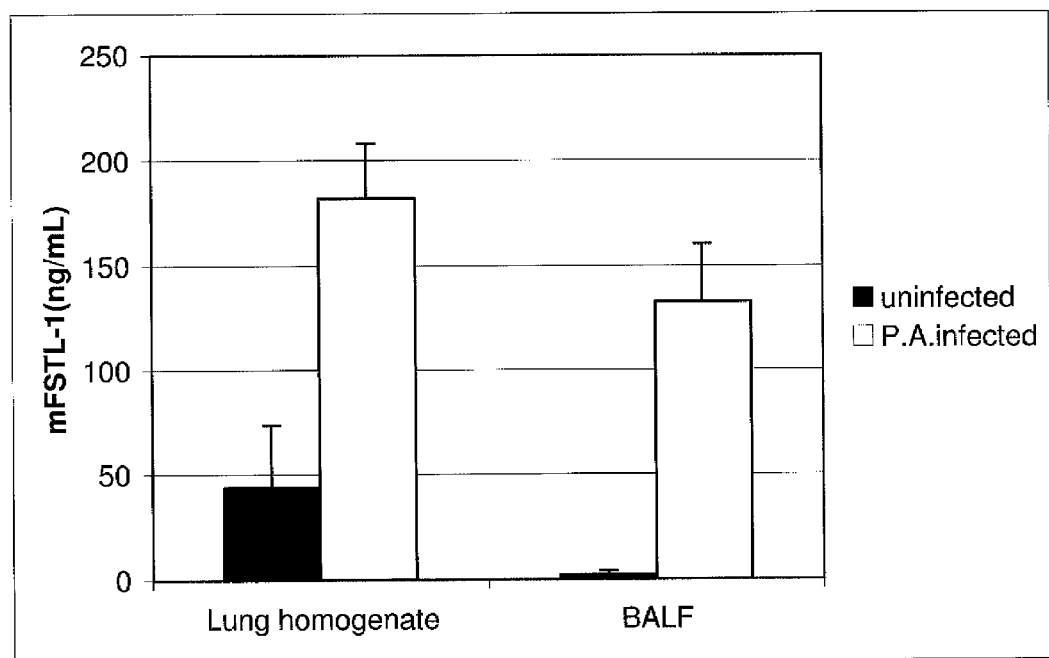
FIG. 6 shows FSTL-1 levels in broncheoalveolar lavage fluid after intratracheal administration of aerosolized *Pseudomonas aeruginosa*.

Mice were administered aerolized *Pseudomonas aeruginosa* intratracheally. Twenty four hours later broncheoalveolar lavage and lung homogenates were assayed for FSTL-1. As shown in FIG. 6, infected mice showed elevated FSTL-1 levels compared to uninfected mice. Thus, this example showed that FSTL-1 could serve as a biomarker for inflammation in an animal model of lung infection.

Example 7

Preparation of Human and Murine FSTL-1 Protein in Bacteria

Human and murine FSTL-1 proteins were prepared in bacteria. The human FSTL-1 gene (GenBank Accession No. BC000055) was cloned into the pGEX-4T-3 GST expression plasmid (Pharmacia, catalog no. 27-4583-01) using the SmaI and NotI restriction sites. The human FSTL-1 PCR product containing these restriction sites, excluding the secretion signal, was generated using the following PCR primers: Forward human FSTL-1 primer containing SmaI site: AACCCGG-GAGGAAGAGCTAAGGAGCAA; Reverse human FSTL-1 primer containing NotI site: TTGCGGCCGCTGTGCCTC-CTCATTAGATCTCTTTGGTGCT. Once the pGEX-4T-3 GST plasmid containing human FSTL-1 was obtained, BL21 bacterial cells were transformed with the plasmid. The GST-tagged FSTL-1 was isolated from the bacterial cells following the manufacturer's protocol.

The murine FSTL-1 protein was prepared similarly to the human protein. The mouse gene (GenBank Accession No. BC028921) was cloned into pGEX-4T-3 using the following murine specific FSTL-1 primers were used: Forward murine FSTL-1 primer containing SmaI site: AACCCGGGAGGAG-GAACCTAGAAGCAA; Reverse murine FSTL-1 primer containing NotI site: TTGCGGCCGCCTGTGCCTCTTCT-TAGATCTCTTTGGTGTT. Once the pGEX-4T-3 GST plasmid containing murine FSTL-1 was obtained, BL21 bacterial cells were transformed with the plasmid. The GST-tagged FSTL-1 was isolated from the bacterial cells following the manufacturer's protocol.

Example 8

Preparation of Murine FSTL-1 Protein in Baculovirus

Murine FSTL-1 was also prepared in insect cells using a baculovirus gene delivery system. The entire murine FSTL-1 cDNA (GenBank Accession No. BC028921) was cloned into the pVL1393 baculovirus transfer plasmid (BD Biosciences, catalog no. 554745) using the XbaI and NotI restriction sites. Following the manufacturers protocol, Sf9 insect cells were infected with the baculovirus expressing the murine FSTL-1 gene. Murine FSTL-1 protein was isolated from the insect cells using a sepharose column containing anti-FSTL-1 antibodies.

Example 9

DNA Microarray Analysis of Mouse Paws

Our initial RPA studies were followed by more detailed studies using DNA microarrays. mRNA was isolated from paws of unimmunized DBA/1 mice, mice at 28 days (early disease), and mice at 49 days (late disease) following primary CII immunization. To obtain sufficient sample for hybridization, mRNA from 4 mice/group were pooled, based on statistical analysis of individual paws in the RPA analysis demonstrating that this number of samples had sufficient power to differentiate between groups. mRNAs were hybridized to Incyte Mouse GEM1 DNA microarrays using a day 1 whole-mouse mRNA preparation as a common reference. Hybridizations were conducted on duplicate chips, allowing for the elimination of genes whose expression levels differed by greater than 50% between the duplicate chips (0.1% of genes). Of 8,734 genes analyzed, 330 were induced and 55 were down-regulated greater than two-fold in early or late disease, at a p value≦0.001, as compared to normal paws. Hierarchical clustering of these genes resulted in five distinct expression patterns (FIG. 7) that correlated with histopathologic changes in the paw. The hierarchical clusters may represent coordinately expressed genes, the effects of cell phenotype, or a combination of the two.

Example 10

Figure 7:
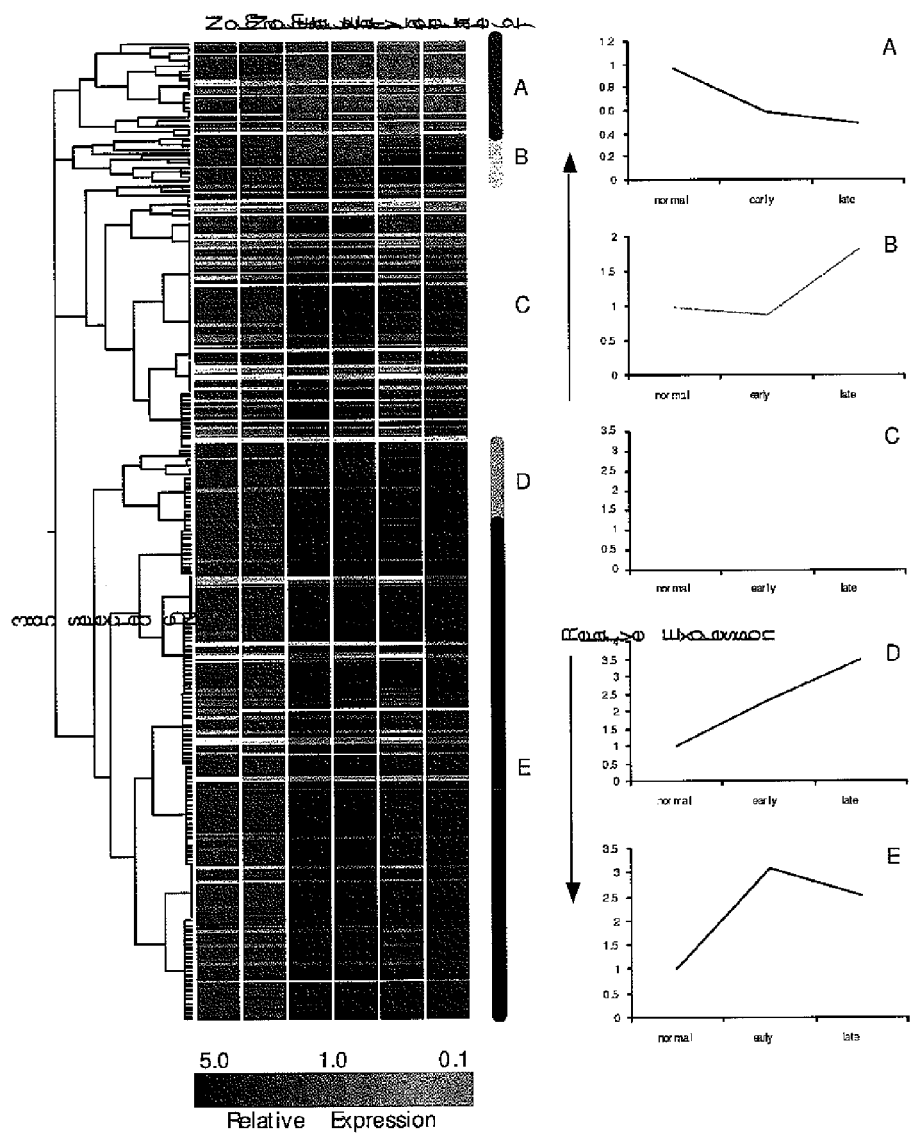
FIG. 7 shows the hierarchical cluster analysis of 385 genes differentially expressed during CIA. The left panel shows the distribution of gene expression across the hierarchical tree structure in which the values for the first normal sample (1) are set to 1. Columns represent individual values of duplicate samples. The intensity from pale to deep indicates trust values. The side bar indicates the five basic clusters of gene expression, with letters corresponding to their grouping. The mean values of all the genes within the indicated groups (A-E) are graphed on the right.
Figure 8:
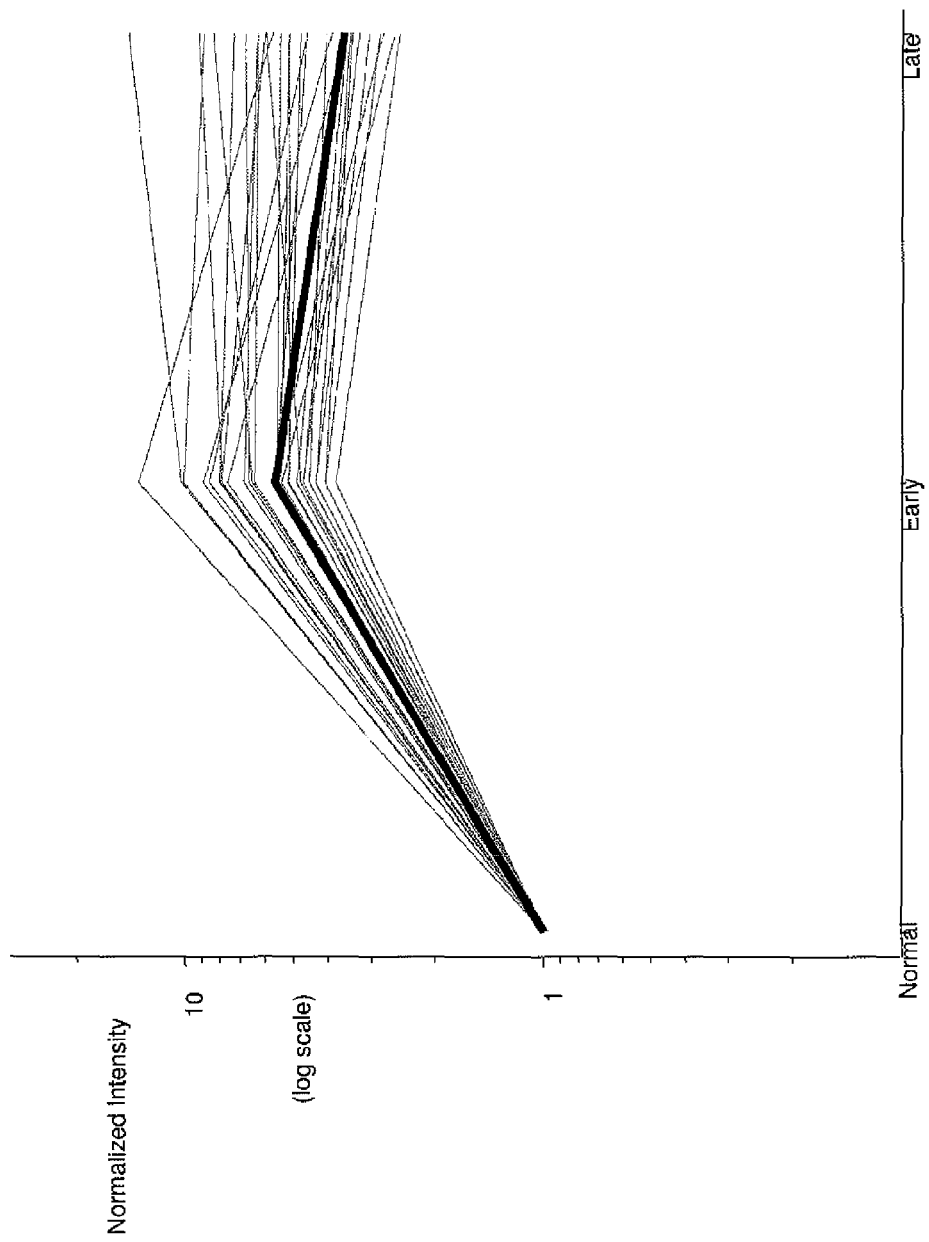
FIG. 8 depicts cluster E genes, shown individually. FSTL-1 is the heavy line.
Figure 9:
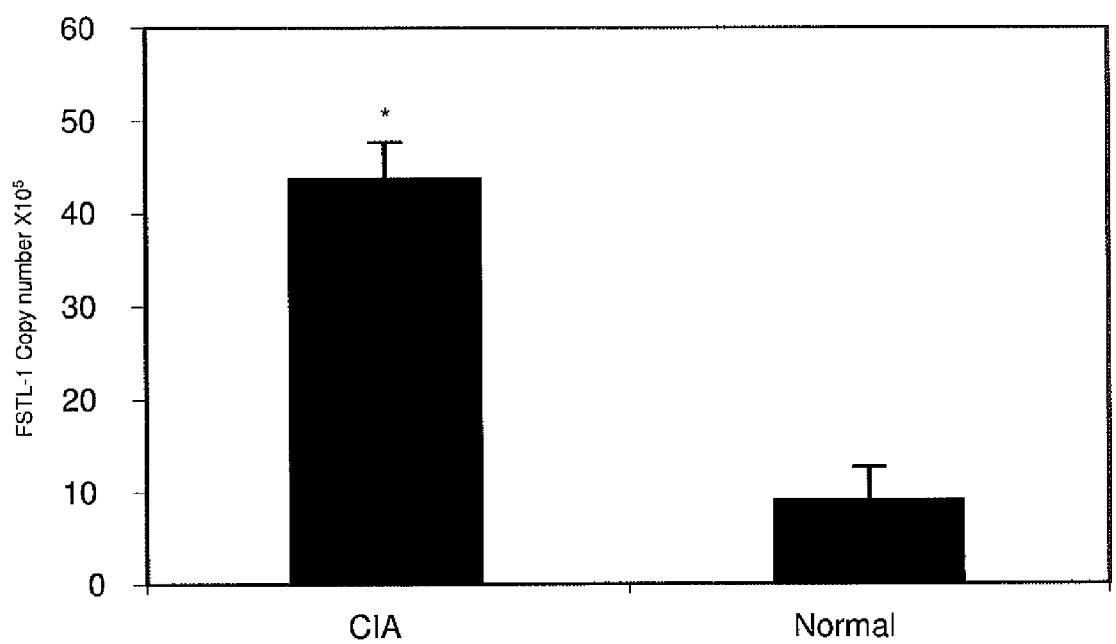
FIG. 9 depicts the results for validation of FSTL-1 microarray data. RNA from normal and CIA (day 35) paws was subjected to real-time PCR analysis. Each bar represents the mean±SEM of 5 paws/group. *p=0.0001

Discovery of a Gene Novel to Arthritis, Follistatin-Like-1 (FSTL-1), by Mining the CIA Gene Expression Dataset In addition to the TGF-β genes, one of the most highly-expressed genes in cluster E (elevated in early and late disease; FIG. 7) was FSTL-1. Expression of FSTL-1 within cluster E is shown in FIG. 8. Confirmation of the microarray data was performed by measuring the expression level of FSTL-1 in five individual paws using real time PCR (FIG. 9). FSTL-1 had been previously cloned from an osteoblast cell line (Shibanuma, M., et al., *Eur J Biochem* 217:13 (1993)). Little had been published on FSTL1 in arthritis, with the exception of a report of autoantibodies to FSTL1 in patients with RA (Tanaka, M., et al., *Int Immunol* 10:1305 (1998)) and a reported inhibition of tumor cell invasiveness by its over-expression (Johnston, I., et al., *Oncogene* 19:5348 (2000)). The similar patterns of expression of TGF-β and FSTL-1 suggested that they might be coregulated and this is supported by the original description of FSTL-1 as a TGF-β-induced gene (Constantinescu, C. S., et al., *J Immunol* 161:5097 (1998)).

Example 11

FSTL-1 is Expressed in CIA and in RA by Fibroblast-Like Synoviocytes (FLS)

Figure 10:
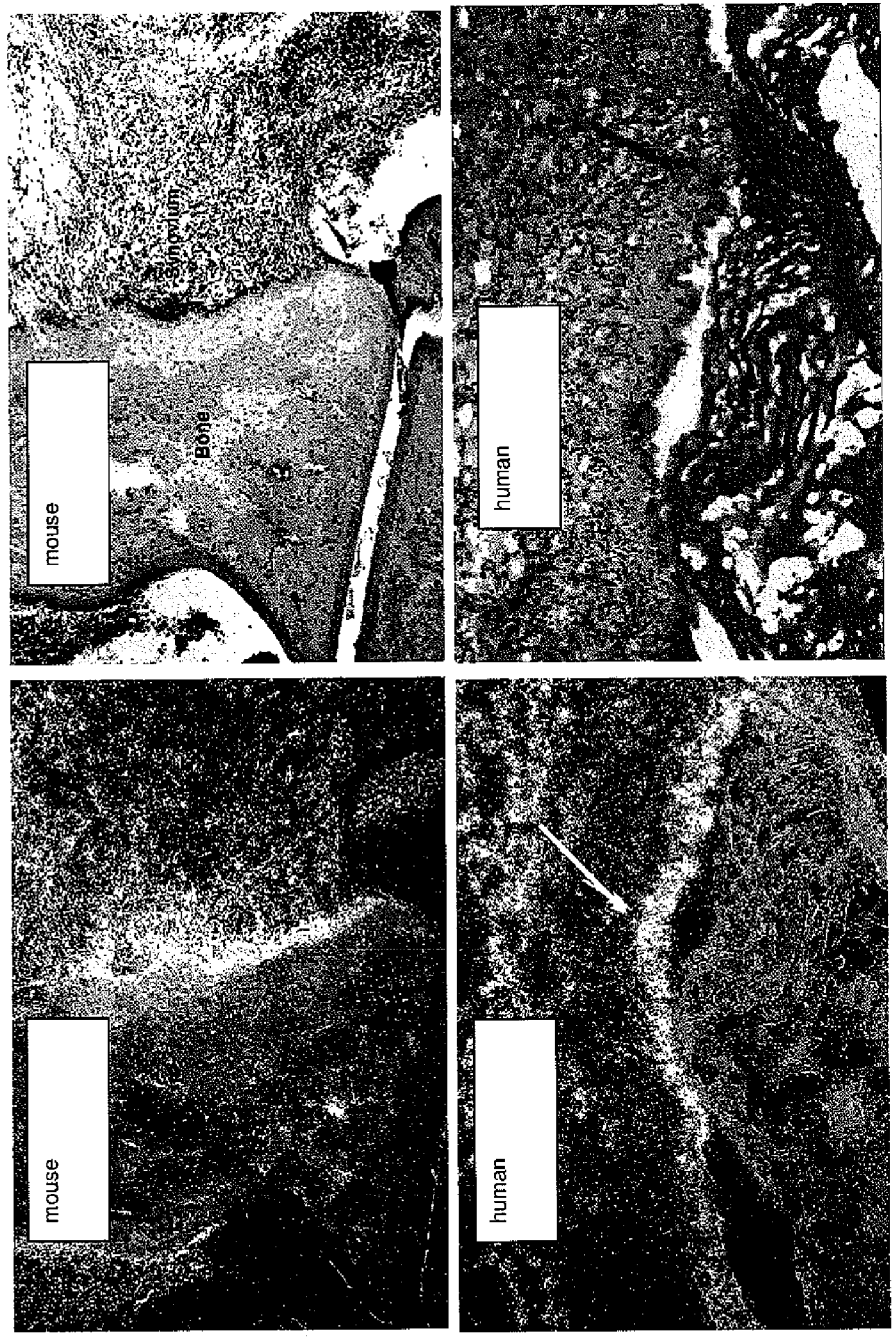
FIG. 10 depicts in situ hybridization demonstrating over-expression of FSTL-1 in synovium in CIA and in the synovial lining (arrow) in human RA. Dark field images are at left and H&E images at right. The area of most intense signal seen in the upper left panel corresponds to the erosive bone margin in the corresponding H&E image in the upper right panel.

We demonstrated by in situ hybridization that FSTL-1 is upregulated throughout the synovial tissue in CIA with particularly-intense staining at the synovial pannus-bone interface near the synovial insertion into bone, adjacent to the articular space, where bone erosion is observed (FIG. 10). This is a common location for erosive changes in arthritis and FIG. 10 demonstrates the most intense FSTL-1 signal in the area of bone erosion. The location suggests that the source might be bone cells, which would be consistent with its original description as an inducible gene in osteoblasts. We did not observe this FSTL-1 expression in normal mouse joints. We have had technical difficulties performing in situ hybridization on human bone because of the need to decalcify them, however, thus far we have demonstrated overexpression of FSTL-1 in the synovial lining in human RA (FIG. 10).

Figure 11:
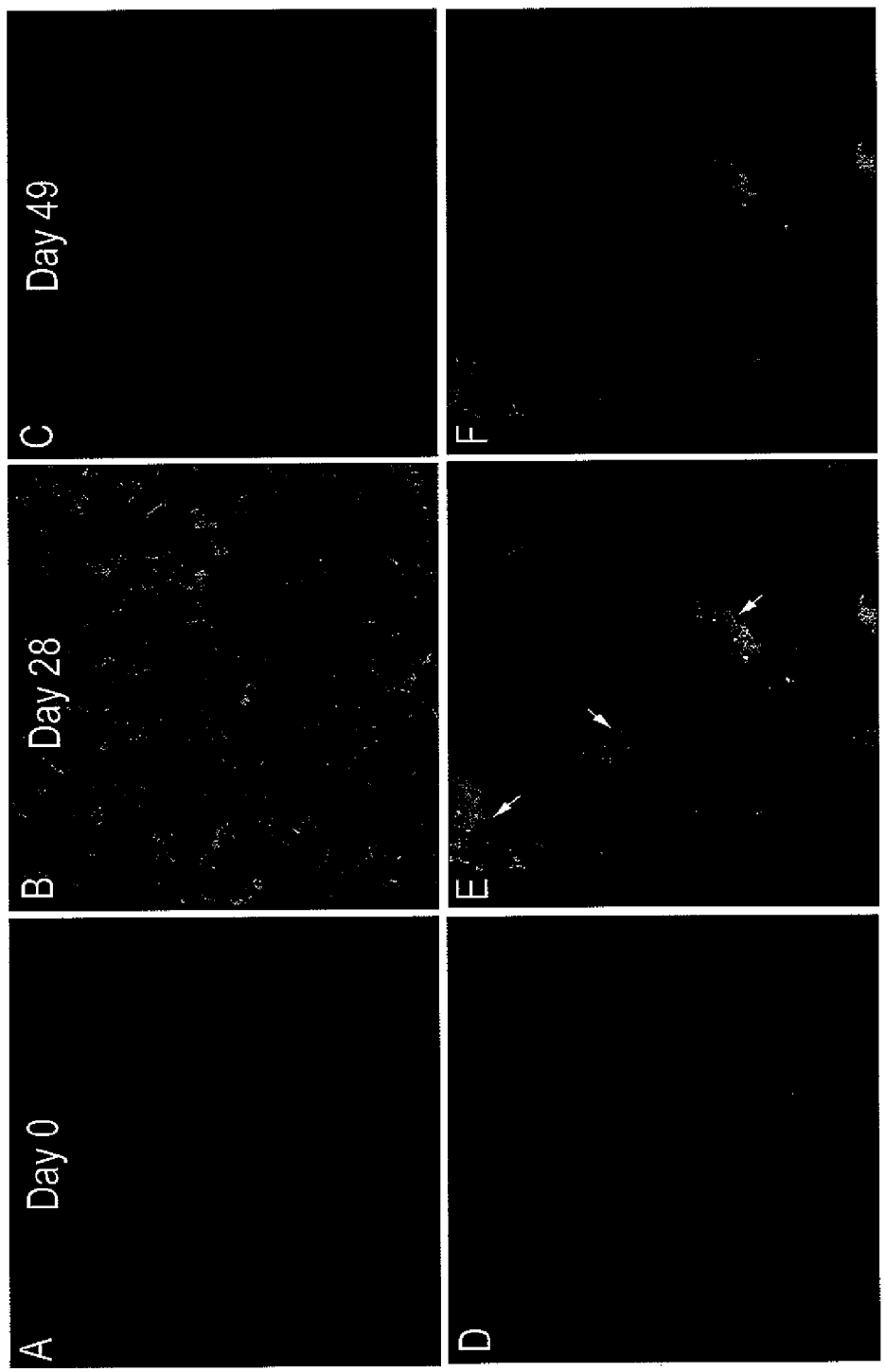
FIG. 11 shows results that FSTL-1 is overexpressed in fibroblast-like synoviocytes in early CIA. Mouse knee joints were harvested from mice prior to immunization with type II collagen (day 0), during acute arthritis (day 28), or during late arthritis (day 49). Tissues were sectioned and stained for FSTL-1 and observed under a confocal microscope at 40× (panels A-C). Higher magnification (100×) views of day 28 synovium show CD90+ fibroblasts in red (D), FSTL-1 in green (F) and colocalization of FSTL-1 with fibroblasts, indicated by the arrows (E).

In 1998, Tanaka et. al. cloned FSTL-1 from rheumatoid arthritis (RA) synovial tissue and demonstrated anti-FSTL-1 antibodies in the serum and synovial fluid of RA patients, and suggested that FSTL-1 was an autoantigen (Tanaka, M., et al., Int Immunol 10:1305 (1998)). To further explore the role of FSTL-1 in arthritis, we examined its cellular distribution in the synovium of mice by immunohistochemistry at various times during the course of arthritis (FIG. 11). Expression of FSTL-1 was observed in fibroblasts, as evidenced by CD-90 staining. No expression was observed in macrophages, neutrophils, or T cells.

Example 12

FSTL-1 is Upregulated in Paws in Response to Complete Freund's Adjuvant (CFA)

Figure 12:
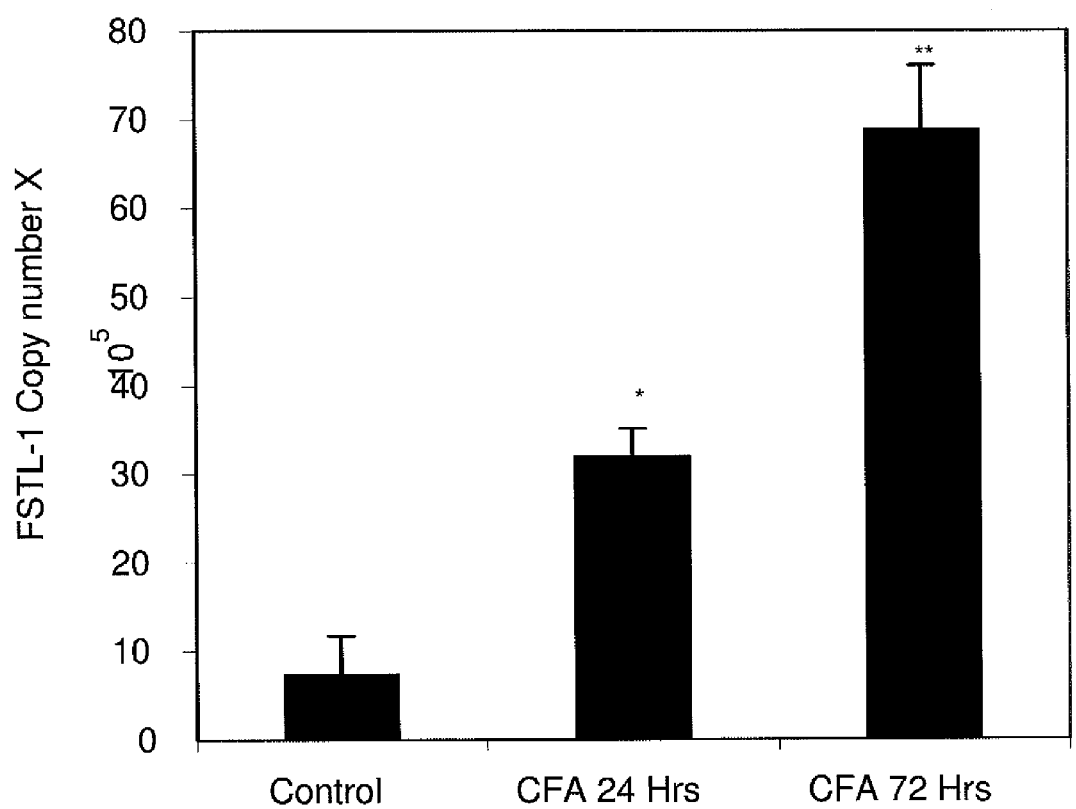
FIG. 12 shows results that FSTL-1 is upregulated in paws in response to CFA. DBA/1 mice were injected intradermally in the paws with 50 µl of CFA. Mice were sacrificed at the indicated times and the paw tissues were homogenized and subjected to real-time PCR analysis. Each bar represents the mean±SEM of 4 paws. No increase was seen in response to injection of buffer (not shown). *p=0.003, **p=0.0003.

To begin to address potential mediators of FSTL-1 expression, mouse paws were injected with CFA. DBA/1 mice were injected intradermally in the paws with 50 µl of CFA. Mice were sacrificed at the indicated times and the paw tissues were homogenized and subjected to real-time PCR analysis. Each bar represents the mean±SEM of 4 paws. No increase was seen in response to injection of buffer. A significant increase in FSTL-1 expression was seen as early as 24 hours later (FIG. 12). These findings suggested that FSTL-1 might also play a role in innate immunity.

Example 13

FSTL-1 is Upregulated in Paws in Response to LPS

Figure 13:
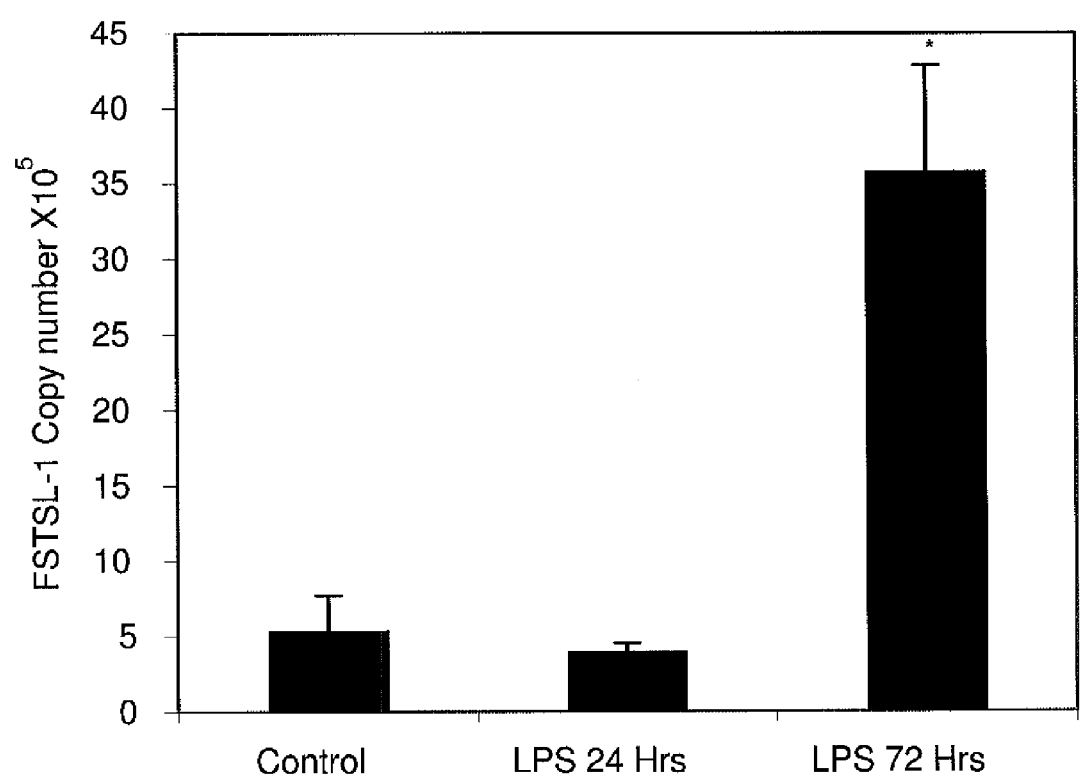
FIG. 13 shows results that FSTL-1 is upregulated in paws in response to LPS. DBA/1 mice were injected intradermally in the paws with 50 µg of LPS. Mice were sacrificed at the indicated times and the paw tissues were homogenized and subjected to real-time PCR analysis. No increase was seen in response to injection of buffer (not shown). Each bar represents the mean±SEM of 4 paws. *p=0.04.

To further test this possibility, we examined FSTL-1 expression following injection of LPS into paws. DBA/1 mice were injected intradermally in the paws with 50 µg of LPS. Mice were sacrificed at the indicated times and the paw tissues were homogenized and subjected to real-time PCR analysis. No increase was seen in response to injection of buffer. Each bar represents the mean±SEM of 4 paws. Within 72 hours of LPS administration, a significant increase in FSTL-1 expression was observed (FIG. 13).

Example 14

Follistatin-Like Protein 1 Promotes Arthritis by Upregulating IFN-γ

References are made to publications in this Example which has the complete bibliographic details after the Examples in the "Reference Bibliography."
Materials and Methods
Adenoviral vectors: A recombinant, E1a-E3-deleted replication defective adenovirus type 5 (Ad5) vector encoding the mouse FSTL-1 gene (NCBI Nucleotide database accession number BC028921) was generated through Cre-lox recombination as described by Hardy et. al. (7). The control vector, Ad-BglII, is an E1a/E3-deleted replication-defective adenovirus type 5 lacking an insert. The vectors were grown in 293 cells and purified by CsCl gradient ultracentrifugation, dialyzed at 4° C. against sterile virus buffer, aliquoted, and stored at −80° C. FSTL-1 expression was verified by both RT-PCR and western blot from infected COS-7 cells.

Mice: Male IFN-γ deficient C.129S7(B6)-Ifng$^{tm1Ts}$/J and wild-type BALB/c mice were purchased from Jackson Laboratory (Bar Harbor, Minn.). Male DBA/1 mice, 6-10 weeks of age, were purchased from Harlan (Indianapolis, Ind.). Mice were housed in the animal resource facility at the Children's Hospital of Pittsburgh Rangos Research Center (Pittsburgh, Pa.). The study was approved by the Children's Hospital of Pittsburgh's Animal Research and Care Committee.

Induction and assessment of arthritis: CIA was induced by intra-dermal immunization of DBA/1 mice with bovine collagen type II (Elastin Products, Owensville, Mo.) and a booster given intraperitoneally 21 days later, as previously described (8). Mice were evaluated for arthritis several times weekly by a blinded observer using a macroscopic scoring system ranging from 0 to 4 (0=no detectable arthritis; 1=swelling and/or redness of paw or 1 digit; 2=2 joints involved; 3=3-4 joints involved; and 4=severe arthritis of entire paw and digits). The arthritic index for each mouse was calculated by adding the score of the 4 individual paws. The statistical significance was determined using the Exact Wilcoxon Test. Paw swelling was measured using calipers. P values<0.05 were considered significant. Some mice were injected in the paws with 1×10$^9$ particles of adenoviral vectors in 50 µl of phosphate buffered saline (PBS). Some mice were treated i.p. with either rabbit IgG (Invitrogen, Carlsbad, Calif.) or with rabbit anti-mouse FSTL-1. This rabbit anti-mouse FSTL-1 was generated through a contract with Invitrogen by immunizing rabbits twice with mouse FSTL-1, bleeding the rabbits, and affinity purifying the serum on an FSTL-1 column.

Quantitative reverse transcriptase-polymerase chain reaction (RT-PCR): Total RNA was isolated from mouse paws or human synovial tissues using Invitrogen's RNA Trizol Reagent (Invitrogen, Carlsbad, Calif.) following the manufacturer's instructions. To remove possible genomic DNA contamination, RNA was treated with DNase I (Ambion, Austin Tex.). Complimentary DNA (cDNA) was synthesized with random hexamer oligonucleotides using 1 µg of RNA and Invitrogen's SuperScript™ II Reverse Transcriptase Kit (Invitrogen, Carlsbad, Calif.). PCR was performed in a Light-Cycler (Mx3000P Stratagene, La Jolla Calif.) using Brilliant® SYBR® Green QPCR Master Mix (Stratagene, La Jolla Calif.) according to the protocol (95° C. hot start for 10 minutes followed by 40 amplification cycles, denaturation at 95° C., primer annealing at 59° C., amplicon extension at 72° C.) using oligonucleotide primer sets for human FSTL-1 (Forward 5' CGATGGACACTGCAAAGAGA-3' Reverse 5'-CCAGCCATCTGGAATGATCT-3'), Mouse FSTL1 (Forward 5'-AACAGCCATCAACATCACCA-3' Reverse 5'-GGCACTTGAGGAACTCTTGG-3'), IFN-γ (Forward 5'-TCAAGTGGCATAGATGTGGAAGAA-3' Reverse 5'-TGGCTCTGCAGGATTTTCATG-3'), and CXCL10 (Forward 5' TGGCTAGTCCTAATTGCCCTTGGT-3' Reverse 5'-TCAGGACCATGGCTTGACCATCAT). The copy number (number of transcripts) of amplified products was calculated from a standard curve obtained by plotting known input concentrations of plasmid DNA.

ELISA: IFN-γ was assayed using commercial reagents (BD Biosciences San Jose, Calif.) according to the manufacturer's instructions. FSTL-1 was assayed by coating Nunc Immunomodule MaxiSorp ELISA plates (Nalgene, Rochester N.Y.) with 100 μl of 2 μg/ml monoclonal rat anti-FSTL-1 (R&D Systems, Minneapolis, Minn.) overnight at 4° C. Plates were washed with PBS/0.05% Tween-20 and blocked with 1% BSA/5% sucrose/0.05% Tween-20 for 1 hour. Samples were added overnight at 4° C. Then 2.5 μg/ml biotin-labeled polyclonal rabbit anti-FSTL-1 was added for 4 hours. Plates were washed and incubated with streptavidin-HRP (Invitrogen, Carlsbad, Calif.), developed with Peroxidase Substrate System ABTS (Kirkegaard & Perry, Gaithersburg, Md.), and absorbance read at 405 nm on a microplate reader.

Induction of FSTL-1: In order to inhibit NFκB, the mouse osteoblast cell line, MC3T3 (9) was infected with a retrovirus encoding a super IκB repressor and containing a puromycin resistance gene (10). Following one week of selection in 2 μg/ml puromycin, confirmation of NF-κB inhibition was determined by transfecting cells with a plasmid encoding the luciferase reporter gene under control of an NFκB responsive element using the Fugene 6 transfection reagent as described by the manufacturer (Roche Diagnostics, Basel, Switzerland). Cells were assayed after 48 hours for luciferase activity using the Promega Bright-Glo Luciferase Assay System according to the manufacturer's instructions (Promega, Madison, Wis.). Luciferase units were measured using a Packard microplate scintillation and luminescence counter. Control and super IκB-expressing MC3T3 cells ($1 \times 10^4$ cells/well) were cultured for 3 days in triplicate in media, TGF-β (2 ng/ml), LPS (100 ng/ml), or IL-1β (10 ng/ml) and supernatants were assayed by ELISA for FSTL-1.

Histological Analysis: Mouse paws were fixed in 10% neutral buffered formalin, decalcified, dehydrated in a gradient of alcohols, paraffin embedded, sectioned, mounted on glass slides, and stained with H&E as previously described (6).

Western blot: Samples of mouse serum (6 μl) or purified FSTL-1 protein generated in bacculovirus (0.15 μg) were mixed with loading buffer containing β-mercaptoethanol and boiled for 10 minutes, then run on a 10-20% Tris Glycine SDS-polyacrylamide gradient gel (Inviogen, Carlsbad Calif.) and transferred overnight onto a nitrocellulose membrane. The membrane was blocked for 1 hour with 5% milk in Tris-Buffered Saline Tween-20 (TBST) at room temperature with agitation. The membrane was probed for 2 hours with 0.4 μg/ml polyclonal rabbit anti-FSTL-1, washed 3× in TBST, and incubated for 1 hour with horse radish peroxidase-labeled goat anti-rabbit Ig that had been pre-absorbed against mouse serum (Thermo Scientific, Rockford Ill.). The membrane was washed 3× with TBST and developed using the SuperSignal West Femto Maximum Sensitivity Substrate (Thermo Scientific, Rockford Ill.). MagicMark XP Western Protein Standard (Invitrogen, Carlsbad Calif.) was used as a molecular weight marker lane.

Results

Figure 14:
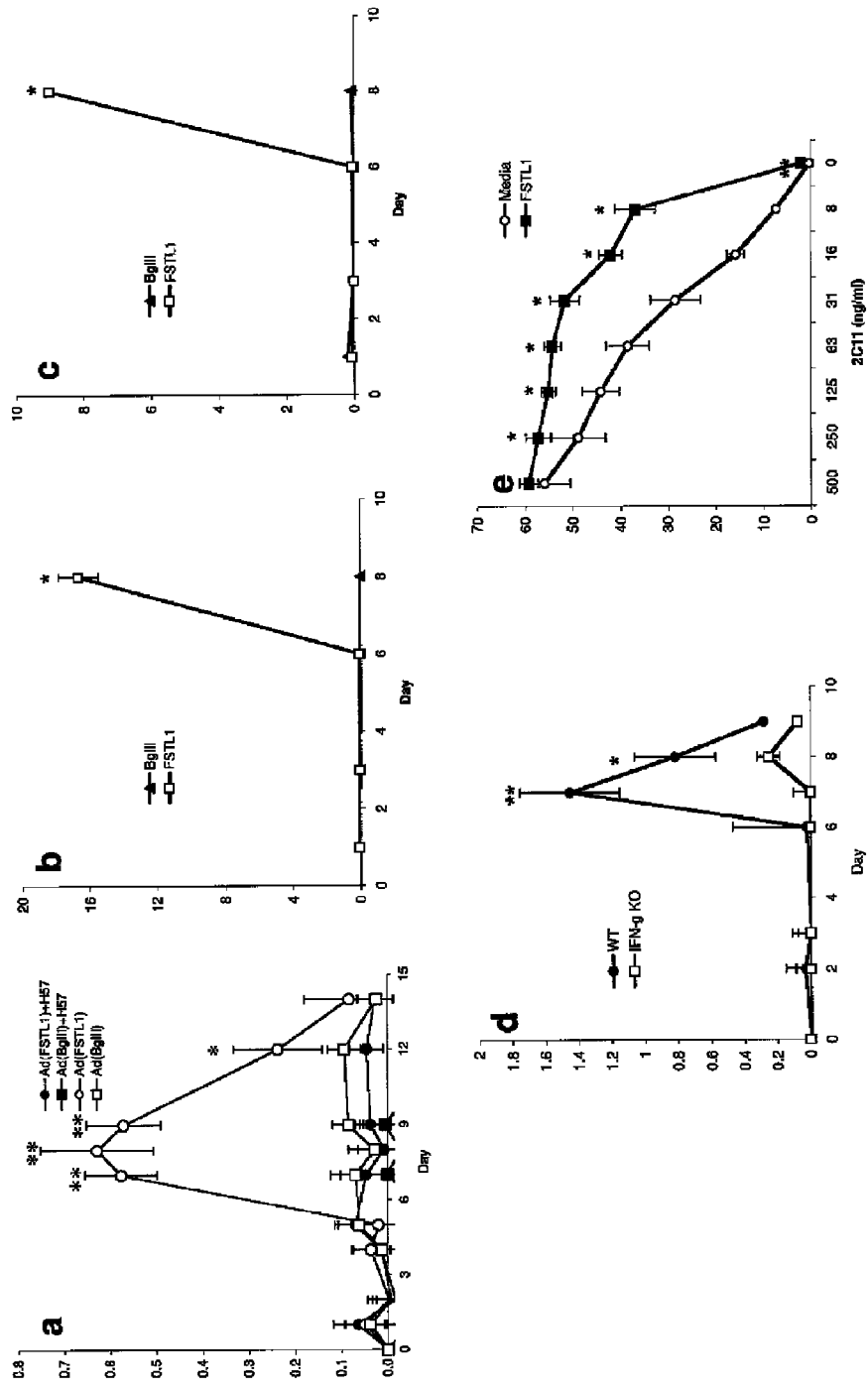
FIG. 14 show results that FSTL-1 enhances T cell IFN-γ production. (a) DBA/1 male mice were injected i.p. with 0.4 mg of the anti-T cell receptor mAb, H57 (black symbols). One week later (day 0), hind paws were injected with $1 \times 10^9$ particles of Ad(FSTL-1) or Ad(BglII). Paw swelling above pre-treatment baseline was measured. The data represents the mean±SEM of 8 paws/group for each condition. T cell depletion of H57-treated mice was confirmed at the end of the study by flow cytometry on spleen cells. P values are shown for Ad(FSTL1) vs. Ad(FSTL1)+H57. A similar group of mice were sacrificed on days 1, 3, 6, and 8 and mRNA from hind paws (n=2/group) was extracted and amplified by real time PCR for IFN-γ (b), CXCL10 (c), or IL-1β (d). (e) IFN-γ knockout mice and wild type BALB/c controls were treated as in (a). The data represents 4 hind paws/group. (f) DBA/1 spleen cells were cultured in media containing 10% fetal calf serum for 3 days with or without FSTL-1 (5 µg/ml) in the presence of the indicated titers of the anti-CD3 mAb, 2C11. Supernatants were assayed for IFN-γ by ELISA. Each bar represents the mean±SEM of triplicate wells. *p<0.05; **p<0.01 by paired t test. Experiments were performed three times to ensure reproducibility.

FSTL-1 enhances T cell IFN-γ production: The inventors previously found that injection of adenovirus encoding FSTL-1 into mouse paws results in severe paw swelling and synovitis (6). To understand how FSTL-1 mediates this effect, the inventors incubated mouse spleen cells with FSTL-1 for 24 hours and performed DNA microarray analysis on mRNA from these cells. Upregulation of a number of IFN-γ-related genes was observed. Since T cells are a major source of IFN-γ, we assessed the ability of FSTL-1 to induce inflammation in mice depleted of mature αβ+ T cells by treatment with the anti-αβ mAb, H57 (11). Hind paws were injected with Ad(FSTL-1) or a control adenovirus, Ad(BglII). Depletion of αβ+ T cells abrogated FSTL-1-induced paw swelling (FIG. 14a). In a separate experiment, hind paws were injected with Ad(FSTL-1) or Ad(BglII) and mice were killed on days 1, 3, 6, and 8 and mRNA from the hind paws was assayed by real time PCR. Message for IFN-γ (FIG. 14b) as well as the IFN-γ-induced chemokine, CXCL10 (FIG. 14e) increased substantially with the appearance of paw swelling, suggesting a central role for IFN-γ. Other proinflammatory cytokines, including IL-1β (FIG. 14d) and TNF-α were also increased. To confirm that FSTL-1 mediates its inflammatory effect through induction of IFN-γ, IFN-γ null mice and wild type controls were administered Ad(FSTL-1). FSTL-1-induced paw swelling was abrogated in mice deficient in IFN-γ (FIG. 14d).

To further explore the ability of FSTL-1 to enhance T cell responses, we incubated mouse spleen cells with purified FSTL-1 protein. FSTL-1 alone induced a small, but statistically-significant, amount of IFN-γ (FIG. 14e). A strong synergistic effect was observed in the presence of a weak T cell receptor signal delivered by low-titer anti-CD3 mAb, 2C11. At a titer of 8 ng/ml of 2C11, co-culture with FSTL-1 increased IFN-γ production by 5-fold. This effect was not observed with purified T cells, indicating that the activity of FSTL-1 requires an accessory cell population.

Figure 15:
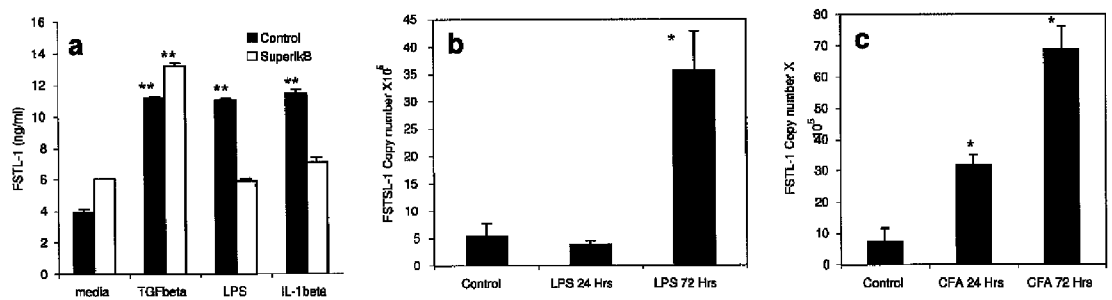
FIG. 15 shows results that FSTL-1 is induced in response to mediators of innate immunity. (a) Control and super IκB-expressing MC3T3 cells were cultured for 3 days in triplicate in media, TGF-β (2 ng/ml), LPS (100 ng/ml), or IL-1β (10 ng/ml) and supernatants were assayed by ELISA for FSTL-1. Each bar represents the mean and SEM and p values are comparing each group's media control. DBA/1 mice were injected intradermally in the paws with 50 µg of LPS (b), 50 µl of CFA (c), or $5 \times 10^8$ particles of Ad(IL-1β) (d). Mice were sacrificed at the indicated times and the paws were subjected to real-time PCR analysis. Each bar represents the mean±SEM of 4 hind paws from 2 mice. No increase was seen in response to injection of buffer (not shown). *p<0.05; **p<0.01 by paired t test. Experiments were performed twice to ensure reproducibility.

FSTL-1 is induced in response to mediators of innate immunity: FSTL-1 was originally described as a TGF-β inducible gene derived from the osteoblast cell line, MC3T3 (2). TGF-β signals through the SMAD pathway (12, 13). However, the ability of FSTL-1 to enhance T cell responses suggested a similarity to NFκB-dependent cytokines, such as TNF-α, that are induced by innate immune signals and can enhance T cell activation (14, 15). To determine whether FSTL-1 is induced by innate signaling, we incubated MC3T3 cells with the TLR4 agonist, LPS, or with IL-1β, both of which signal through the NFκB pathway. Both LPS and IL-1β induced FSTL-1 (FIG. 15a). A second group of MC3T3 cells were infected with a retrovirus encoding a super IκB inhibitor, in which the IκBα molecule is mutated. The mutation prevents the molecule from being phosphorylated by IκB kinase and subsequently degraded, which is normally required for the translocation of NFκB to the nucleus (16). To confirm that NFκB was inhibited, the cells were transfected with a reporter plasmid containing an NFκB responsive element and encoding luciferase. Two days hours after transfection, luciferase activity was measured. The cells containing the inhibitor had approximately 10-fold lower luciferase activity (data not shown), indicating that NFκB activation was impaired. These super-IκB-expressing MC3T3 cells lost the ability to produce FSTL-1 in response to LPS and IL-1β, while still responding to TGF-β, demonstrating that FSTL-1 can be induced through NFκB in addition to SMAD. We observed a similar induction of FSTL-1 in vivo following injection of LPS (FIG. 15b) or IL-1β (FIG. 15d) into mouse paws, as well as injection of complete Freund's adjuvant (FIG. 15c).

Figure 16:
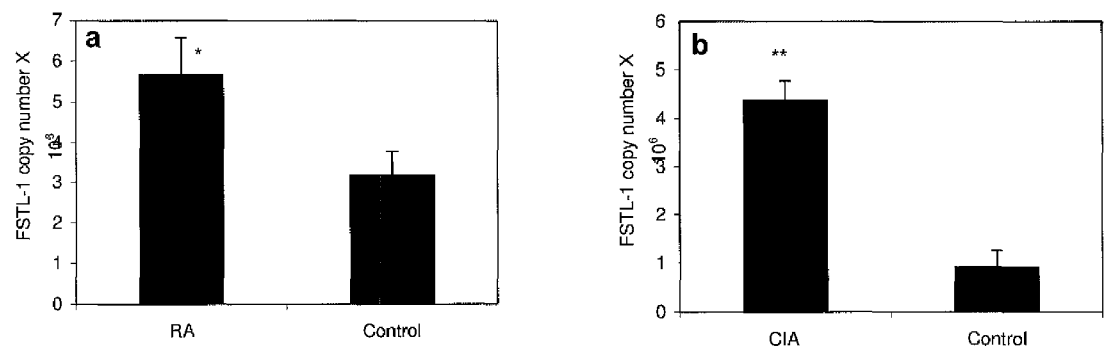
FIG. 16 shows results that FSTL-1 is over-expressed in RA and CIA synovium. (a) Human synovial tissues from RA patients (n=5) or control patients undergoing knee arthroscopic ACL repair (n=12), and (b) paws from CIA mice on day 35 or untreated controls (5 paws/group) were subjected to real-time PCR for FSTL-1 mRNA. Each bar represents the mean±SEM. *p=0.03; **p=0.0001 by paired t test.

FSTL-1 is over-expressed in rheumatoid arthritis (RA) synovium: We have previously found FSTL-1 mRNA in RA synovial tissues (1). To determine whether this expression was constitutive, or reflected active synovitis, RA synovial tissues were assayed by real-time PCR. RA synovium had a 2-fold increase in FSTL-1 mRNA, compared to control synovium obtained from patients undergoing knee arthroscopic ACL repair (FIG. 16a). The magnitude of this increase was similar to the induction of FSTL-1 mRNA in the paws of mice with CIA (FIG. 16b). This finding is also consistent with a previous report suggesting that FSTL-1 is overexpressed by 2-3 fold in human RA synovial tissue, as compared to tissue from osteoarthritis (17). Together, these findings provide strong evidence for a role of FSTL-1 in human RA.

Endogenously produced FSTL-1 plays a role in CIA: We have demonstrated that administration of FSTL-1 by gene transfer exacerbates CIA (6), demonstrating that exogenously administered FSTL-1 could exacerbate arthritis. To determine whether endogenous FSTL-1 plays a role in CIA, we generated and affinity purified rabbit anti-mouse FSTL-1 IgG and used it to neutralize FSTL-1 activity in vivo. DBA/1 mice were immunized with type II collagen (CII) on days 0 and 21 to induce CIA. On days 20, 22, 24, 26, and 28, mice were injected i.p. with 200 μg of either rabbit anti-FSTL-1 antibody or with rabbit IgG as a control. A third group of mice received no antibody. A substantial reduction of arthritis was observed in mice treated with anti-FSTL-1 antibody (FIG. 17a-c), indicating that endogenous FSTL-1 does indeed play a pro-inflammatory role in CIA, as its neutralization ameliorates arthritis. The incidence of arthritis was not reduced.

Figure 17:
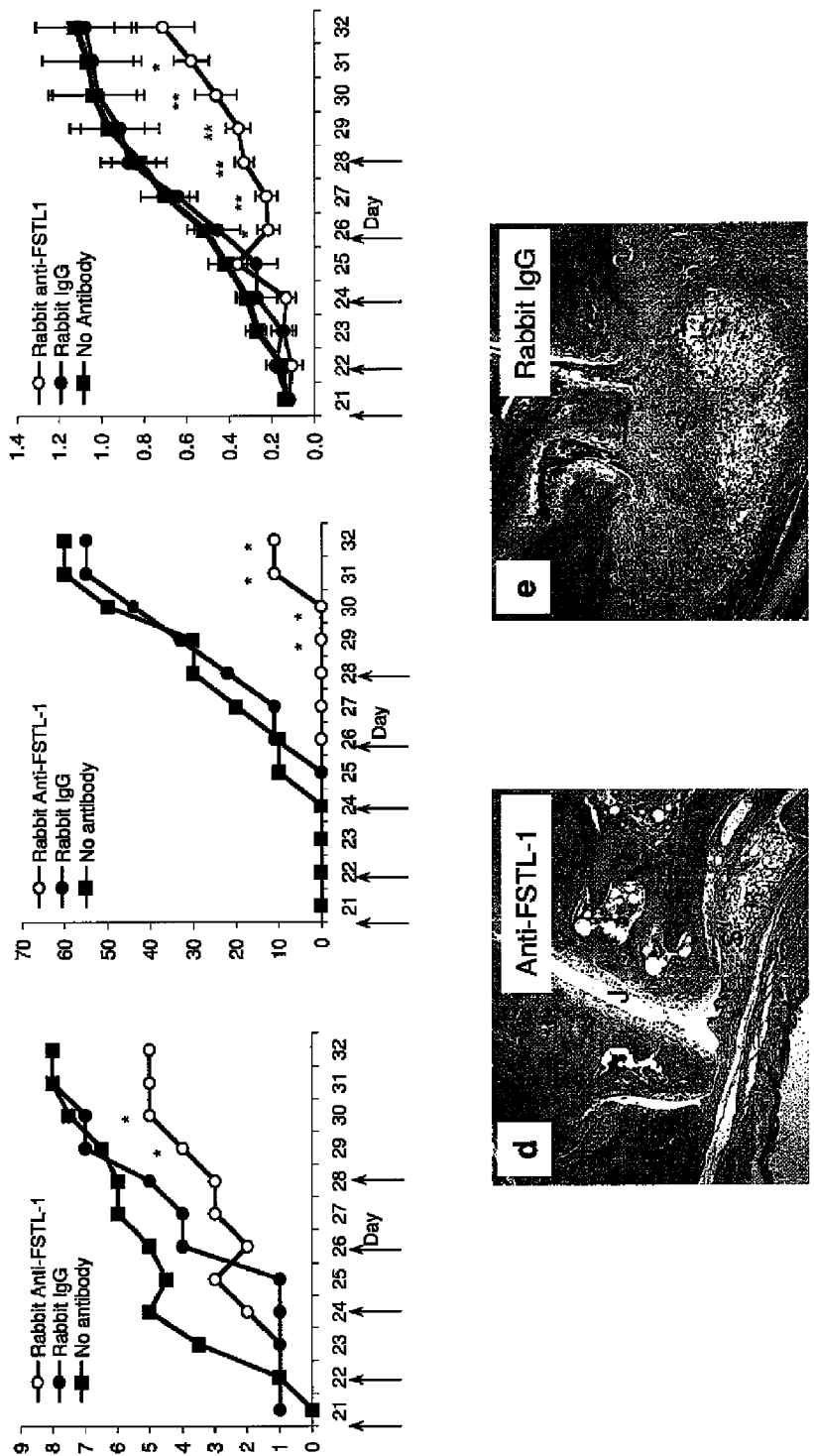
FIG. 17 shows results that neutralization of endogenous FSTL-1 suppresses CIA. Affinity purified polyclonal rabbit anti-mouse FSTL-1 was shown to bind specifically to mouse FSTL1 by Western blot (a) where lane 1 is a molecular weight marker standard, lane 2 is 0.15 µg of purified mouse FSTL1 protein generated in Sf9 cells, lane 3 is 6 µl of day 2 serum from a DBA/1 mouse treated with 1×10$^9$ particles of Ad(FSTL-1), and lane 4 is serum from a DBA/1 mouse treated with the control Ad(BglII). Mice were immunized with CII on days 0 and 21 and injected i.p. on the days indicated by the arrows with 200 µg of rabbit anti-FSTL-1 IgG or polyclonal rabbit IgG as a control (9 mice per group). A third group received no antibody. The hind paw arthritic index (b), the % of mice with a maximum arthritic index of 16 (c), and paw swelling above pre-immunization baseline (d), were scored by a blinded observer. P values are shown for anti-FSTL-1 vs. rabbit IgG and were performed by paired t test except for (b) which was by Exact Wilcoxon test. (e) Hind paws from unimmunized mice (control) or from day 35 CII-immunized mice treated with anti-FSTL-1 or rabbit IgG (n=6 mice/group) were subjected to real-time PCR for IFN-γ, CXCL1β and mRNA. Each bar represents the mean±SEM. Severe synovitis with destruction of cartilage and bone can be seen in representative day 35 paw sections from rabbit IgG-treated mice (f), while joints of anti-FSTL-1-treated mice (g) are well preserved. J=joint, S=synovium (magnification× 100). *p<0.05; **p<0.01.

Analysis of paws demonstrated increased mRNA for IFN-γ CXCL10, and IL-1β on day 35 of CIA (FIG. 17d). All of these were significantly reduced, down to baseline expression, in mice treated with anti-FSTL-1. These results support the conclusion from FIG. 14 that FSTL-1 upregulates IFN-γ and related genes. This finding is especially relevant to arthritis, since it has recently been demonstrated that CXCL10 is a central mediator of bone erosion in CIA (18). Bone and cartilage erosion was found to be substantially reduced in CIA following treatment of mice with anti-FSTL1 (FIGS. 17e and 17f).

Discussion

We have reported that over-expression of FSTL-1 by gene transfer exacerbates mouse CIA (6), demonstrating that exogenously administered FSTL-1 could exacerbate arthritis. The data disclosed herein shows conclusively that endogenous FSTL-1 plays a pro-inflammatory role in CIA, as its neutralization ameliorates arthritis. Our finding that FSTL-1 is upregulated in RA synovial tissues indicates that this is also applicable to human RA. Furthermore, human and mouse FSTL-1 share 92% identity in their amino acid sequences.

These results shed further light on the possible mechanism of action of FSTL-1. Without being bound by theory, FSTL-1 by itself has limited ability to induce IFN-γ. However, in the context of T cell activating signals, it functions to upregulate IFN-γ secretion. In vitro, we observed that FSTL-1 dramatically increases IFN-γ secretion when T cell are stimulated with a weak signal provided by low-dose anti-CD3. Therefore a similar mechanism of action may occur in vivo. Paw swelling in response to Ad(FSTL-1) is only observed a week after injection. This would be explained if sufficient activated T cells need to reach the paws in response to adenovirus infection before FSTL-1 can act. This would also explain why FSTL-1, which is constitutively expressed at low levels in the joint (1), does not induce inflammation in the normal situation. The pro-inflammatory effect of FSTL-1 would require the presence of activated T cells.

Without being bound by theory, these results indicate that FSTL-1 is induced by innate immune mediators central to arthritis. IL-1β is an especially important arthritis-promoting cytokine and its ability to induce FSTL-1 might explain the upregulation of FSTL-1 observed in both mouse and human arthritic joints (1). The increased FSTL-1 would then be available to act upon activated T cells, leading to further inflammation. Thus, FSTL-1 may function as a bridge between innate and adaptive immune responses by being produced in response to innate signals and then amplifying T cell responses. In this fashion, it might function analogously to TNF which can promote T cell responses (14, 15). It has been suggested that signal strength drives T cells through hierarchical thresholds associated with proliferation preceding the acquisition of fitness and effector functions (19, 20). At the two extremes are anergy after a very weak signal strength and activation-induced cell death after excessive stimulation. The stimulation strength is determined by at least three independent parameters (antigen dose, co-stimulation and duration). FSTL-1 may function to enhance stimulation strength following T cell activation, thereby helping to drive T cells to a mature effector state.

We have shown that IFN-γ protects against CIA when given prior to disease onset but exacerbates CIA when given after disease onset (21, 22) consistent with the observation that IFN-γ deficient mice on the C57BL/6 background are more susceptible than wild-type C57BL/6 (23). Thus induction of IFN-γ by FSTL-1 would be a reasonable mechanism to explain its arthritogenic effect.

In summary, we provide evidence that FSTL-1 is a novel arthritogenic protein that plays a central role in arthritis through promotion of T cell activation and induction of IFN-γ.

REFERENCES BIBLIOGRAPHY

1. Thornton, S., D. Sowders, B. Aronow, D. P. Witte, H. I. Brunner, E. H. Giannini, and R. Hirsch. 2002. DNA microarray analysis reveals novel gene expression profiles in collagen-induced arthritis. *Clin Immunol* 105:155-168.
2. Shibanuma, M., J. Mashimo, A. Mita, T. Kuroki, and K. Nose. 1993. Cloning from a mouse osteoblastic cell line of a set of transforming-growth-factor-beta 1-regulated genes, one of which seems to encode a follistatin-related polypeptide. *Eur J Biochem* 217:13-19.
3. Tanaka, M., S. Ozaki, F. Osakada, K. Mori, M. Okubo, and K. Nakao. 1998. Cloning of follistatin-related protein as a novel autoantigen in systemic rheumatic diseases. *Int Immunol* 10:1305-1314.
4. Kawabata, D., M. Tanaka, T. Fujii, H. Umehara, Y. Fujita, H. Yoshifuji, T. Mimori, and S. Ozaki. 2004. Ameliorative effects of follistatin-related protein/TSC-36/FSTL1 on joint inflammation in a mouse model of arthritis. *Arthritis Rheum* 50:660-668.
5. Tanaka, M., S. Ozaki, D. Kawabata, M. Kishimura, F. Osakada, M. Okubo, M. Murakami, K. Nakao, and T. Mimori. 2003. Potential preventive effects of follistatin-related protein/TSC-36 on joint destruction and antagonistic modulation of its autoantibodies in rheumatoid arthritis. *Int Immunol* 15:71-77.
6. Miyamae, T., A. D. Marinov, D. Sowders, D. C. Wilson, J. Devlin, R. Boudreau, P. Robbins, and R. Hirsch. 2006. Follistatin-like protein-1 is a novel proinflammatory molecule. *J Immunol* 177:4758-4762.
7. Hardy, S., M. Kitamura, T. Harris-Stansil, Y. Dai, and M. L. Phipps. 1997. Construction of adenovirus vectors through Cre-lox recombination. *J Virol* 71:1842-1849.
8. Hughes, C., J. A. Wolos, E. H. Giannini, and R. Hirsch. 1994. Induction of T cell anergy in an experimental model of autoimmunity using non-mitogenic anti-CD3 monoclonal antibody. *J Immunol* 153:3319-3325.
9. Sudo, H., H. A. Kodama, Y. Amagai, S. Yamamoto, and S. Kasai. 1983. In vitro differentiation and calcification in a new clonal osteogenic cell line derived from newborn mouse calvaria. *J Cell Biol* 96:191-198.
10. Shin, S. R., N. Sanchez-Velar, D. H. Sherr, and G. E. Sonenshein. 2006. 7,12-dimethylbenz(a)anthracene treatment of a c-rel mouse mammary tumor cell line induces epithelial to mesenchymal transition via activation of nuclear factor-kappaB. *Cancer Res* 66:2570-2575.
11. Kubo, R. T., W. Born, J. W. Kappler, P. Marrack, and M. Pigeon. 1989. Characterization of a monoclonal antibody which detects all murine αβ T cell receptors. *J Immunol* 142:2736-2742.
12. Massague, J., and Y. G. Chen. 2000. Controlling TGF-beta signaling. *Genes Dev* 14:627-644.
13. Moustakas, A. 2002. Smad signalling network. *J Cell Sci* 115:3355-3356.
14. Kim, E. Y., and H. S. Teh. 2001. TNF type 2 receptor (p75) lowers the threshold of T cell activation. *J Immunol* 167:6812-6820.
15. Yamada, A., A. D. Salama, N. Najafian, H. Auchincloss, Jr., and M. H. Sayegh. 2001. TNF:TNF-R costimulatory pathways in transplantation. *Transplant Proc* 33:3070-3071.
16. Brown, K., S. Gerstberger, L. Carlson, G. Franzoso, and U. Siebenlist. 1995. Control of I kappa B-alpha proteolysis by site-specific, signal-induced phosphorylation. *Science* 267:1485-1488.
17. Ehara, Y., D. Sakurai, N. Tsuchiya, K. Nakano, Y. Tanaka, A. Yamaguchi, and K. Tokunaga. 2004. Follistatin-related protein gene (FRP) is expressed in the synovial tissues of rheumatoid arthritis, but its polymorphisms are not associated with genetic susceptibility. *Clin Exp Rheumatol* 22:707-712.
18. Kwak, H. B., H. Ha, H. N. Kim, J. H. Lee, H. S. Kim, S. Lee, H. M. Kim, J. Y. Kim, H. H. Kim, Y. W. Song, and Z. H. Lee. 2008. Reciprocal cross-talk between RANKL and interferon-gamma-inducible protein 10 is responsible for bone-erosive experimental arthritis. *Arthritis Rheum* 58:1332-1342.
19. Gett, A. V., F. Sallusto, A. Lanzavecchia, and J. Geginat. 2003. T cell fitness determined by signal strength. *Nat Immunol* 4:355-360.
20. van Stipdonk, M. J., G. Hardenberg, M. S. Bijker, E. E. Lemmens, N. M. Droin, D. R. Green, and S. P. Schoenberger. 2003. Dynamic programming of CD8+ T lymphocyte responses. *Nat Immunol* 4:361-365.
21. Thornton, S., G. P. Boivin, K. N. Kim, F. D. Finkelman, and R. Hirsch. 2000. Heterogeneous effects of IL-2 on collagen-induced arthritis. *J Immunol* 165:1557-1563.
22. Thornton, S., K. A. Kuhn, F. D. Finkelman, and R. Hirsch. 2001. NK cells secrete high levels of IFN-gamma in response to in vivo administration of IL-2. *European journal of immunology* 31:3355-3360.
23. Chu, C. Q., Z. Song, L. Mayton, B. Wu, and P. H. Wooley. 2003. IFNgamma deficient C57BL/6 (H-2b) mice develop collagen induced arthritis with predominant usage of T cell receptor Vbeta6 and Vbeta8 in arthritic joints. *Annals of the rheumatic diseases* 62:983-990.

What is claimed is:

1. A method for diagnosing systemic juvenile rheumatoid arthritis in an individual comprising: (a) measuring the level of protein expression of follistatin-like protein-1 in a biological sample collected from the individual; and (b) comparing the level of protein expression of follistatin-like protein-1 in the sample from the individual with the level of follistatin-like protein 1 in a healthy subject, where an increased level of follistatin-like protein-1 in the individual sample relative to the healthy subject, wherein the individual exhibits joint swelling, indicates that the individual has a diagnosis of systemic juvenile rheumatoid arthritis.

2. A method for diagnosing Kawasaki's disease in an individual comprising: (a) measuring the level of protein expression of follistatin-like protein-1 in a biological sample collected from the individual; and (b) comparing the level of protein expression of follistatin-like protein-1 in the sample from the individual with the level of follistatin-like protein 1 in a healthy subject, where an increased level of follistatin-like protein-1 in the individual sample relative to the healthy subject, wherein the individual exhibits one or more symptom selected from the group consisting of eye redness, rash on stomach, chest and genitals, red and dry lips, swollen tongue, coated tongue, sore throat, swollen palms, swollen soles of feet, swollen lymph nodes, and combinations thereof, indicates that the individual has a diagnosis of Kawasaki's disease.

3. The method according to claim 1 wherein the level of follistatin-like protein-1 is measured by enzyme linked immunosorbent assay.

4. The method according to claim 2 wherein the level of follistatin-like protein-1 is measured by enzyme linked immunosorbent assay.

* * * * *

UNITED STATES PATENT AND TRADEMARK OFFICE
CERTIFICATE OF CORRECTION

PATENT NO.        : 8,211,652 B2
APPLICATION NO.   : 12/864709
DATED             : July 3, 2012
INVENTOR(S)       : Raphael Hirsch It is certified that error appears in the above-identified patent and that said Letters Patent is hereby corrected as shown below:

Title Page at heading (54) and Column 1 Title: FSTL-1 AS A BIOMAKER OF INFLAMMATION should read

-- FSTL-1 AS A BIOMARKER OF INFLAMMATION --

Signed and Sealed this
Twenty-eighth Day of August, 2012

David J. Kappos
*Director of the United States Patent and Trademark Office*

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 1
aacccgggag gaagagctaa ggagcaa                                          27

<210> SEQ ID NO 2
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 2
ttgcggccgc tgtgcctcct cattagatct ctttggtgct                           40

<210> SEQ ID NO 3
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 3
aacccgggag gaggaaccta gaagcaa                                          27

<210> SEQ ID NO 4
<211> LENGTH: 40
<212> TYPE: DNA
<213> ORGANISM: Artificial sequence
<220> FEATURE:
```

```
<223> OTHER INFORMATION: Synthetic oligonucleotide

<400> SEQUENCE: 4
ttgcggccgc ctgtgcctct tcttagatct ctttggtgtt                                40

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
cgatggacac tgcaaagaga                                                      20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
ccagccatct ggaatgatct                                                      20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
aacagccatc aacatcacca                                                      20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ggcacttgag gaactcttgg                                                      20

<210> SEQ ID NO 9
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 9
tcaagtggca tagatgtgga agaa                                                 24

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
tggctctgca ggattttcat g                                                    21

<210> SEQ ID NO 11
```

```
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 11
tggctagtcc taattgccct tggt                                          24

<210> SEQ ID NO 12
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 12
tcaggaccat ggcttgacca tcat                                          24
```